US009157915B2

(12) United States Patent
Gerna et al.

(10) Patent No.: US 9,157,915 B2
(45) Date of Patent: *Oct. 13, 2015

(54) DEVICES AND METHODS FOR DETECTING HUMAN METAPNEUMOVIRUS

(71) Applicant: Diagnostic Hybrids, Inc., Athens, OH (US)

(72) Inventors: Giuseppe Gerna, Pavia (IT); Antonella Sarasini, Stradella (IT); Maria Grazia Revello, Albiolo (IT)

(73) Assignee: DIAGNOSTIC HYBRIDS, INC., Athens, OH (US)

( * ) Notice: Subject to any disclaimer, the term of this patent is extended or adjusted under 35 U.S.C. 154(b) by 82 days.

This patent is subject to a terminal disclaimer.

(21) Appl. No.: 13/945,716

(22) Filed: Jul. 18, 2013

(65) Prior Publication Data

US 2014/0024549 A1    Jan. 23, 2014

Related U.S. Application Data

(63) Continuation of application No. 11/409,600, filed on Apr. 24, 2006, now Pat. No. 8,492,097.

(51) Int. Cl.
| | | |
|---|---|---|
| *G01N 33/53* | (2006.01) | |
| *G01N 33/569* | (2006.01) | |
| *G01N 33/577* | (2006.01) | |
| *C07K 16/10* | (2006.01) | |

(52) U.S. Cl.
CPC ...... *G01N 33/56983* (2013.01); *C07K 16/1027* (2013.01); *G01N 2333/115* (2013.01)

(58) Field of Classification Search
None
See application file for complete search history.

(56) References Cited

U.S. PATENT DOCUMENTS

| | | | |
|---|---|---|---|
| 4,458,066 A | 7/1984 | Caruthers et al. | 536/25.34 |
| 4,683,195 A | 7/1987 | Mullis et al. | 435/6 |
| 4,683,202 A | 7/1987 | Mullis | 435/91.2 |
| 4,795,698 A | 1/1989 | Owen et al. | 435/4 |
| 4,800,159 A | 1/1989 | Mullis et al. | 435/91.2 |
| 4,816,567 A | 3/1989 | Cabilly et al. | 530/387.3 |
| 4,965,188 A | 10/1990 | Mullis et al. | 435/6 |
| 5,707,850 A | 1/1998 | Cole et al. | 435/239 |
| 5,885,470 A | 3/1999 | Parce et al. | 216/33 |
| 6,444,461 B1 | 9/2002 | Knapp et al. | 435/283.1 |
| 6,765,088 B1 | 7/2004 | Korth et al. | 530/388.1 |
| 6,843,781 B2 | 1/2005 | Alchas et al. | 604/117 |
| 8,492,097 B2 * | 7/2013 | Gerna et al. | 435/7.1 |
| 2003/0232326 A1 | 12/2003 | Fouchier et al. | 435/5 |
| 2004/0005544 A1 | 1/2004 | Fouchier et al. | 435/5 |
| 2005/0053919 A1 | 3/2005 | De Jong et al. | 435/5 |

FOREIGN PATENT DOCUMENTS

WO    WO 02/057302    7/2002

OTHER PUBLICATIONS

Gerna et al. 2006 J Clinical Virology, vol. 35, pp. 113-116.*
Barany, et al., "Solid-phase peptide synthesis;" pp. 3-284, In: The Peptides: Analysis, Synthesis, Biology. vol. 2: Special Methods in Peptide Synthesis, Part A, pp. 3-199 (1962).
Barany, et al., "Solid-phase peptide synthesis;" pp. 3-284, In: The Peptides: Analysis, Synthesis, Biology. vol. 2: Special Methods in Peptide Synthesis, Part A, pp. 200-284 (1962).
Bastien, et al., "Sequence analysis of the N, P, M, and F genes of Canadian human *metapneumovirus*." *Virus Res.*, 93:51-62 (2003).
Beaucage, et al. "Deoxynucleoside phosphoramidites—A new class of key intermediates for deoxypolynucleotide synthesis." *Tetrahedron Letts.*, 22:1859-1862 (1981).
Boivin, et al. "Global genetic diversity of human *metapneumovirus* fusion gene." *Emerg. Infect. Dis.*, 10:1154-1157 (2004).
Boivin, et al. "Virological features and clinical manifestations associated with human *pneumovirus*: A new paramyxovirus responsible for acute respiratory-tract infections in all age groups." *J. Infect. Dis.*, 186: 1330-1334 (2002).
Brown, et al. "Chemical synthesis and cloning of a tyrosine tRNA gene." *Meth. Enzymol.*, 68:109-151 (1979).
Ebihara, et al. "Detection of human *metapneumovirus* antigens in nasopharyngeal secretions by an immunofluorescent-antibody test." *J. Clin. Microbiol.*, 43:1138-1141 (2005).
Gema, et al. "Changing circulation rate of human *metapneumovirus* strains and types among hospitalized pediatric patients during three consecutive winter-spring seasons." *Arch. Virol.*, 150:2365-2375 (2005).
Gema, et al. "Simultaneous detection and typing of human *metapneumovirus* strains in nasopharyngeal secretions and cell cultures by monoclonal antibodies." *J. Clin. Virol.*, 35:113-115 (2006).
Griffiths, et al. "Human anti-self antibodies with high specificity from phage display libraries." *Embo J.*, 12:725-734 (1993).
Hoogenboom, et al. "Multi-subunit proteins on the surface of filamentous phage: methodologies for displaying antibody (Fab) heavy and light chains." *Nucleic Acids Res.*, 19:4133-4137 (1991).
Huse, et al. "Generation of a large combinatorial library of the immunoglobulin repertoire in phage lambda." *Science*, 246:1275-1281 (1989).

(Continued)

*Primary Examiner* — Mary E Mosher
*Assistant Examiner* — Myron Hill
(74) *Attorney, Agent, or Firm* — Medlen & Carroll, LLP

(57) ABSTRACT

The present invention discloses specific human metapneumovirus monoclonal antibodies. The antibody is at least two-fold less reactive with non-human metapneumoviruses including, but not limited to, respiratory viruses or avian metapneumoviruses. Further, the antibody is at least two-fold more reactive with a human metapneumovirus (i.e., for example, Type A or Type B) than with non-human metapneumoviruses including, but not limited to, respiratory viruses or avian metapneumoviruses. Consequently, these novel antibodies are useful as a clinical diagnostic agent, especially when using fresh nasopharengeal aspirates. The invention also contemplates numerous diagnostic platforms that together with the novel antibodies can support economical, fast, and highly selective detection and identification of clinical inoculum samples.

**44 Claims, 4

(56) References Cited

OTHER PUBLICATIONS

Jacobs, et al. "Subtype B avian *metapneumovirus* resembles subtype A more closely than subtype C or human *metapneumovirus* with respect to the phosphoprotein, and second matrix and small hydrophobic proteins." *Virus Res.*, 92:171-178 (2003).
Jones, et al. "Replacing the complementarity-determining regions in a human antibody with those from a mouse." *Nature*, 321:522-525 (1986).
Kohler, et al. "Derivation of specific antibody-producing tissue culture and tumor lines by cell fusion." *Eur. J. Immunol.*, 6:511-519 (1976).
Landry, et al. "Detection of human *metapneumovirus* in clinical samples by immunofluorescence staining of shell vial centrifugation cultures prepared from three different cell lines." *J. Clin. Microbiol.*, 43:1950-1952 (2005).
Mackay, et al. "Use of the P gene to genotype human *metapneumovirus* identifies 4 viral subtypes." *J. Infect. Dis.*, 190:1913-1918 (2004).
Marks, et al. "By-passing immunization: Human antibodies from V-gene libraries displayed on phage." *J. Mol. Biol.*, 22:581-597 (1991).
Maxam, et al. "Sequencing end-labeled DNA with base-specific chemical cleavages." *Meth. Enzymol.*, 65:499-560 (1980).
McCafferty, et al. "Phage antibodies: filamentous phage displaying antibody variable domains." *Natur*, 348:552-554 (1990).
Merrifield, et al. "Solid Phase Peptide Synthesis." *J. Am. Chem. Soc.*, 85:2149-2154 (1963).
Narang, et al. Improved phosphotriester method for the synthesis of gene fragments. *Meth. Enzymol.*, 68:90-99 (1979).
Needham-VanDevanter, et al. "Characterization of an adduct between CC-1065 and a defined oligodeoxynucleotide duplex." *Nucleic Acids Res.*, 12:6159-6168 (1984).
Newman, et al. "Sequence analysis of the Washington/1964 strain of human parainfluenza virus type 1 (HPIV1) and recovery and characterization of wild-type recombinant HPIV1 produced by reverse genetics." *Virus Genes*, 24:77-92 (2002).
Njenga, et al. "*Metapneumovirus* in birds and humans." *Virus Res.*, 91:163-169 (2003).
Pearson, et al. "High-performance anion-exchange chromatography of oligonucleotides." *J. Chrom.*, 255:137-149 (1983).
Percivalle, et al. "Rapid detection of human metapneumovirus strains in nasopharyngeal aspirates and shell vial cultures by monoclonal antibodies." *J. Clin. Microbiol.*, 43:34433446 (2005).
Peret, et al. Characterization of human *metapneumoviruses* isolated from patients in North America,: *J. Infect. Dis.*, 185:1660-1663 (2002).
Rovida, et al. "Monoclonal antibodies versus reverse transcription-PCR for detection of respiratory viruses in a patient population with respiratory tract infections admitted to hospital." *J. Med. Virol.*, 75:336-347 (2005).
Sararini, et al. "Detection and pathogenicity of human *metapneumovirus* respiratory infection in pediatric Italian patients during a winter-spring season." *J. Clin. Virol.*, 35:59-68 (2006).
Scott, et al. "Automated elution electrophoresis: a potential clinical tool." *Clin. Chem.*, 21(9):1217-20 (1975).
Skipadopoulos, et al. "The two major human *metapneumovirus* genetic lineages are highly related antigenically, and the fusion (F) protein is a major contributor to this antigenic relatedness." *J. Virol*., 78:6927-6937 (2004).
Van den Hoogen, et al. "Antigenic and genetic variability of human *metapneumoviruses*." *Emerg. Infect. Dis*., 10:658-665 (2004).
Van den Hoogen, et al. "A newly discovered human pneumovirus isolated from young children with respiratory tract disease." *Nat. Med*., 7:719-724 (2001).
Van de Hoogen, et al. "Prevalence and clinical symptoms of human *metapneumovirus* infection in hospitalized patients." *J. Infect. Dis*., 188:1571-1577 (2003).

* cited by examiner

DEVICES AND METHODS FOR DETECTING HUMAN METAPNEUMOVIRUS

FIELD OF INVENTION

This invention is related to the detection and identification of viruses. In one embodiment, the virus comprises a metapneumovirus. In one embodiment, the virus infects a mammal. In one embodiment, the infection may be identified using an antibody. In particular, the antibodies are monoclonal antibodies produced from a hybridoma cell culture.

BACKGROUND

The human metapneumovirus (hMPV) had been present in the human population for at least 50 years before it was first identified. *Nature Medicine* 7:P719-724 (2001). hMPV belongs to the Paramyxoviridae family of viruses, which includes several well known human pathogens such as measles virus, mumps virus, parainfluenza viruses and the human respiratory syncytial virus (hRSV). Based on hMPV's genetic sequence and structure, hMPV falls in the Pneumovirinae sub-family, together with its closest known human-infecting relative, Respiratory Syncytial Virus (RSV). However, hMPV's genetic sequence and structure differs sufficiently from that of RSV and is consequently placed in a separate genus—the Metapneumoviruses.

hMPV infects people of all ages and causes mild to severe respiratory infections. By the age of 5, most children have been infected with hMPV at least once. Severe disease requiring hospitalization occurs primarily in young children, the elderly and the immunocompromised. hMPV's clinical impact and epidemiology is very similar to that of RSV and infection by these two viruses cannot be distinguished on the bases of clinical signs alone.

Human metapneumovirus is common worldwide and seems to be most active in late winter and early spring—a period when many other respiratory viruses are also circulating. Several epidemiological surveys on hMPV infection have documented cases of metapneumovirus in Europe, Africa, Asia/Australia, Southern America, and Northern America. Worldwide, hMPV accounts for a significant portion of respiratory tract illnesses in hospitalized children, with high incidences occurring during the winter months in moderate climate zones and late spring-early summer in the subtropics. hMPV accounts for roughly 5 to 15% of the respiratory tract illnesses in hospitalized young children, with children <2 years of age being most at risk for serious hMPV infections. hMPV infections, like RSV and influenza virus infections, also account for respiratory tract infections in the elderly population and in patients with underlying disease.

What is needed is a simple, fast, and economical method to detect and identify types and subtypes of human metapneumovirus without the implementation of cell culture protocols, and without cross-reactivity to avian metapneumoviruses.

SUMMARY

This invention is related to the detection and identification of viruses. In one embodiment, the virus comprises a metapneumovirus. In one embodiment, the virus infects a mammal. In one embodiment, the infection may be identified using an antibody. In particular, the antibodies are monoclonal antibodies produced from a hybridoma cell culture.

In one embodiment, the present invention contemplates a composition, comprising: a) a monoclonal antibody having specificity for a human metapneumovirus, wherein said antibody is at least two-fold less reactive with a virus selected from the group consisting of respiratory virus and avian metapneumovirus; and b) a binding partner, wherein said partner is capable of interacting with said antibody. In one embodiment, the antibody is specific for Type A human metapneumovirus. In one embodiment, the antibody is specific for Type B human metapneumovirus. In one embodiment, the binding partner comprises an epitope selected from the group consisting of protein L, protein N, protein F, and protein P. In one embodiment, the binding partner comprises an epitope selected from the group consisting of protein L, protein N, protein F, and protein P. In one embodiment, the binding partner is a protein. In one embodiment, the binding partner is a nucleic acid. In one embodiment, the protein is a protein derived from a human metapneumovirus.

In one embodiment, the present invention contemplates a composition, comprising: a) a monoclonal antibody having specificity for a human metapneumovirus, wherein said antibody is at least two-fold more reactive with said human metapneumovirus than a second virus selected from the group consisting of respiratory virus and avian metapneumovirus; and b) a binding partner, wherein said partner is capable of interacting with said antibody under conditions that is at least two-fold more reactive than a second virus selected from the group comprising respiratory virus or avian metapneumovirus. In one embodiment, the antibody is specific for Type A human metapneumovirus. In one embodiment, the antibody is specific for Type B human metapneumovirus. In one embodiment, the binding partner comprises an epitope selected from the group consisting of protein L, protein N, protein F, and protein P. In one embodiment, the binding partner comprises an epitope selected from the group consisting of protein L, protein N, protein F, and protein P. In one embodiment, the binding partner is a protein. In one embodiment, the binding partner is a nucleic acid. In one embodiment, the protein is a protein derived from a human metapneumovirus.

In one embodiment, the present invention contemplates a panel, comprising a first and second monoclonal antibodies to human metapneumovirus, wherein said antibodies are at least two-fold less reactive with a second virus selected from the group consisting of respiratory virus and avian metapneumovirus. In one embodiment, the first antibody is specific for Type A human metapneumovirus. In one embodiment, the second antibody is specific for Type B human metapneumovirus. In one embodiment, the first antibody binds to an epitope selected from the group consisting of protein L, protein N, protein F, and protein. P. In one embodiment, the second antibody binds to an epitope selected from the group consisting of protein L, protein N, protein F, and protein P.

In one embodiment, the present invention contemplates a monoclonal antibody having specificity for a human metapneumovirus, wherein said antibody is at least two-fold less reactive with a second virus selected from the group consisting of respiratory virus and avian metapneumovirus. In one embodiment, the antibody is specific for Type A human metapneumovirus. In one embodiment, the antibody is specific for Type B human metapneumovirus. In one embodiment, the antibody binds to an epitope selected from the group consisting of protein L, protein N, protein F, and protein P. In one embodiment, the antibody binds to an epitope selected from the group consisting of protein L, protein N, protein F, and protein P.

In one embodiment, the present invention contemplates a monoclonal antibody having specificity for a human metapneumovirus, wherein said antibody is at least two-fold more reactive with said human metapneumovirus than a second virus selected from the group consisting of respiratory virus and avian metapneumovirus. In one embodiment, the antibody is specific for Type A human metapneumovirus. In one embodiment, the antibody is specific for Type B human metapneumovirus. In one embodiment, the antibody binds to an epitope selected from the group consisting of protein L, protein N, protein F, and protein P. In one embodiment, the antibody binds to an epitope selected from the group consisting of protein L, protein N, protein F, and protein P.

In one embodiment, the present invention contemplates a method, comprising: a) providing; i) an animal comprising spleen cells; ii) an inoculum comprising human metapneumovirus; and iii) a cultured cell capable of fusing with said spleen cells; b) immunizing said animal with said inoculum so as to create an immunized animal; c) isolating at least a portion of said spleen cells from said immunized animal; d) fusing said spleen cell with said cultured cell such that a hybridoma cell culture is produced, wherein said cell culture produces a monoclonal antibody having reactivity with said human metapneumovirus, wherein said antibody is at least two-fold less reactive with a second virus selected from the group consisting of respiratory virus and avian metapneumovirus, or preferably, said antibody is two-fold more reactive with said human metapneumovirus than with said second virus selected from the group comprising respiratory virus or avian metapneumovirus. In one embodiment, the animal is a mouse. In one embodiment, the human metapneumovirus comprises Type A human metapneumovirus. In one embodiment, the human metapneumovirus comprises Type B human metapneumovirus. In one embodiment, the inoculum comprises a nasopharangeal aspirate. In one embodiment, the aspirate is collected from a human. In one embodiment, the antibody is specific for Type A human metapneumovirus. In one embodiment, the antibody is specific for Type B human metapneumovirus. In one embodiment, the antibody binds to an epitope selected from the group consisting of protein L, protein N, protein F, and protein P.

DEFINITIONS

The term "antibody", as used herein, refers to any polypeptide substantially encoded by an immunoglobulin gene or immunoglobulin genes, or fragments thereof which specifically bind and recognize an analyte (antigen). The recognized immunoglobulin genes include the kappa, lambda, alpha, gamma, delta, epsilon and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. An antibody may be of animal (especially mouse or rat) or human origin or may be chimeric or humanized.

The term "hMPV antibody", as used herein, refers to any antibody or antibody fragment that specifically binds a polypeptide encoded by the human metapneumovirus genome, cDNA, or a subsequence thereof, or a glycolipid (i.e., a lipid comprising an attached sugar residue).

The term "susceptible to infection", as used herein, refers to the ability of a cell to become infected with virus or another intracellular organism. Although it encompasses "permissive" infections, it is not intended that the term be so limited, as it is intended that the term encompass circumstances in which a cell is infected, but the organism does not necessarily replicate and/or spread from the infected cell to other cells. The phrase "viral proliferation," as used herein describes the spread or passage of infectious virus from a permissive cell type to additional cells of either a permissive or susceptible character.

The term, "humanized antibody", as used herein, refer to any chimeric immunoglobulins, immunoglobulin chains or fragments thereof (such as Fv, Fab, Fab', $F(ab')_2$ or other antigen-binding subsequences of antibodies). Humanized antibodies include human immunoglobulins (recipient antibody) in which residues from a complementary determining region (CDR) of the recipient are replaced by residues from a CDR of a non-human species (donor antibody) such as mouse, rat or rabbit having the desired specificity, affinity and capacity. In some instances, Fv framework residues of the human immunoglobulin are replaced by corresponding non-human residues. Humanized antibodies may also comprise residues which are found neither in the recipient antibody nor in the imported CDR or framework sequences. In general, the humanized antibody will comprise substantially all of at least one, and typically two, variable domains, in which all or substantially all of the CDR regions correspond to those of a non-human immunoglobulin and all or substantially all of the FR regions are those of a human immunoglobulin consensus sequence. The humanized antibody optimally also will comprise at least a portion of an immunoglobulin constant region (Fe), typically that of a human immunoglobulin. Jones et al., Nature, 321:522-525 (1986). Generally, a humanized antibody has one or more amino acid residues introduced into it from a source which is non-human. Accordingly, such "humanized" antibodies are chimeric antibodies (U.S. Pat. No. 4,816,567; herein incorporated by reference), wherein substantially less than an intact human variable domain has been substituted by the corresponding sequence from a non-human species.

The term "chimeric antibody", as used herein, refers to any antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

The term "epitope", as used herein, refers to any molecular region on the surface of an antigen capable of eliciting an immune response and of combining with the specific antibody produced by such a response. For example, an antigen may comprise amino acids (i.e., for example, a protein or peptide) or nucleic acids (i.e., for example, an oligonucleic acid, ribonucleic acid etc.)

The term "immunoassay", as used herein, refers to any assay that uses an antibody to specifically bind an analyte. The immunoassay is characterized by the use of specific binding properties of a particular antibody to isolate, target, and/or quantify the analyte.

The phrase "specifically (or selectively) binds to an antibody" or "specifically (or selectively) immunoreactive with," when referring to a protein or peptide, as used herein, refers to any binding reaction that is determinative of the presence of the protein in a heterogeneous population of proteins and other biologics. Thus, under designated immunoassay conditions, the specified antibodies bind to a particular protein under conditions such that any binding to other proteins present in the sample is at least two-fold less, preferably at least ten-fold less, and more preferably one hundred-fold less. Specific binding to an antibody under such conditions may require an antibody that is selected for its specificity for a particular protein. For example, antibodies raised an hMPV can be selected to obtain antibodies specifically immunoreactive with that protein and not with other proteins, except for polymorphic variants. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, Antibodies, A Laboratory Manual (1988), for a description of immunoassay formats and conditions that can be used to determine specific immunoreactivity). Typically a specific or selective reaction will be at least twice background signal or noise and more typically more than 10 to 100 times background.

The term "inoculating suspension,", "inoculum, or "inoculant", as used herein, refers to any suspension which may be inoculated with organisms to be tested. It is not intended that the term "inoculating suspension," be limited to a particular fluid or liquid substance. For example, inoculating suspensions may be comprised of water, saline, or an aqueous solution. It is also contemplated that an inoculating suspension may include a component to which water, saline or any aqueous material is added. It is contemplated in one embodiment, that the component comprises at least one component useful for the intended microorganism. It is not intended that the present invention be limited to a particular component.

The terms "sample" and "specimen", as used herein, include any composition that is obtained and/or derived from biological or environmental source, as well as sampling devices (e.g., swabs) which are brought into contact with biological or environmental samples. "Biological samples" include those obtained from an animal (including humans, domestic animals, as well as feral or wild animals, such as ungulates, bear, fish, lagamorphs, rodents, etc.), body fluids such as urine, blood, fecal matter, cerebrospinal fluid (CSF), semen, sputum, and saliva, as well as solid tissue. Also included are samples obtained from food products and food ingredients such as dairy items, vegetables, meat, meat byproducts, and waste. "Environmental samples" include environmental material such as surface matter, soil, water, and industrial materials, as well as material obtained from food and dairy processing instruments, apparatus, equipment, disposable, and non-disposable items. These examples are not to be construed as limiting the sample types applicable to the present invention.

The term "culture", as used herein, refers to any composition, whether liquid, gel, or solid, which contains one or more microorganisms and/or one or more cells. A culture of organisms and/or cells can be pure or mixed. For example, a "pure culture" of an organism as used herein refers to a culture in which the organisms present are of only one strain of a single species of a particular genus. This is in contrast to a "mixed culture" of organisms which refers to a culture in which more than one strain of a single genus and/or species of microorganism is present.

The terms "culture media," and "cell culture media," as used herein, refer to any media that are suitable to support maintenance and/or growth of cells in vitro (i.e., cell cultures).

The term "animal", as used herein, refers to any organism that is capable of becoming immunized by a viral particle (i.e., for example, an hMPV viral particle). For example, an animal may include, but is not limited to, human, dog, cat, cattle, sheep, mice, rats, goats etc.

The term "primary cell", as used herein, refers to any cell which is directly obtained from a tissue or organ of a host whether or not the cell is in culture.

The term "cultured cell", as used herein, refers to any cell which has been maintained and/or propagated in vitro. Cultured cells include primary cultured cells and cell lines.

The term "primary cultured cells", as used herein, refers to any primary cells which are in in vitro culture and which preferably, though not necessarily, are capable of undergoing ten or fewer passages in in vitro culture before senescence and/or cessation of proliferation.

The terms "cell line" and "immortalized cell", as used herein, refers to any cell which is capable of a greater number of cell divisions in vitro before cessation of proliferation and/or senescence as compared to a primary cell from the same source. A cell line includes, but does not require, that the cells be capable of an infinite number of cell divisions in culture. The number of cell divisions may be determined by the number of times a cell population may be passaged (i.e., subcultured) in in vitro culture. Passaging of cells is accomplished by methods known in the art. Briefly, a confluent or subconfluent population of cells which is adhered to a solid substrate (e.g., plastic Petri dish) is released from the substrate (e.g., by enzymatic digestion), and a proportion (e.g., 10%) of the released cells is seeded onto a fresh substrate. The cells are allowed to adhere to the substrate, and to proliferate in the presence of appropriate culture medium. The ability of adhered cells to proliferate may be determined visually by observing increased coverage of the solid substrate over a period of time by the adhered cells. Alternatively, proliferation of adhered cells may be determined by maintaining the initially adhered cells on the solid support over a period of time, removing and counting the adhered cells and observing an increase in the number of maintained adhered cells as compared to the number of initially adhered cells.

The terms "cytopathic effect" or "CPE" as used herein, describe changes in cellular structure (i.e., a pathologic effect). Common cytopathic effects include cell destruction, syncytia (i.e., fused giant cells) formation, cell rounding, vacuole formation, and formation of inclusion bodies. CPE results from actions of a virus on permissive cells that negatively affect the ability of the permissive cellular host to preform its required functions to remain viable. In in vitro cell culture systems, CPE is evident when cells, as part of a confluent monolayer, show regions of non-confluence after contact with a specimen that contains a virus. The observed microscopic effect is generally focal in nature and the foci are initiated by a single virion. However, depending upon viral load in the sample, CPE may be observed throughout the monolayer after a sufficient period of incubation. Cells demonstrating viral induced CPE usually change morphology to a rounded shape, and over a prolonged period of time can die and be released form their anchorage points in the monolayer. When many cells reach the point of focal destruction, the area is called a viral plaque, which appears as a hole in the monolayer. The terms "plaque" and "focus of viral infection" refer to a defined area of CPE which is usually the result of infection of the cell monolayer with a single infectious virus which then replicates and spreads to adjacent cells of the monolayer. Cytopathic effects are readily discernable and distinguishable by those skilled in the art.

The term "hybridoma(s)," as used herein, refers to cells produced by fusing two cell types together. Commonly used hybridomas include those created by the fusion of antibody-secreting B cells from an immunized animal, with a malignant myeloma cell line capable of indefinite growth in vitro. For example, a spleen cell from an immunized animal may be fused together with Ps2/0Ag14 myeloma cell that can be cloned and used to prepare monoclonal antibodies (i.e., for example, hMPV MAbs).

A "target analyte" is any molecule or molecules that are to be detected and/or quantified in a sample. For example, target analytes may include biomolecules including, but not limited to, nucleic acids, antibodies, proteins, sugars, and the like. In particular, a target analyte would include a human metapneumovirus protein and/or nucleic acid.

The terms "binding partner" or "member of a binding pair" refer to molecules that specifically bind other molecules to form a binding complex such as antibody-antigen, lectin-carbohydrate, nucleic acid-nucleic acid, biotin-avidin, etc. The binding complex is predominantly mediated by non-covalent (e.g. ionic, hydrophobic, etc.) interactions. The terms "binding partner" and "member of a binding pair" apply to individual molecules, as well as to a set of multiple copies of such molecules, e.g., affixed to a distinct location of a surface. Thus, as used herein, the expression "different binding partners" includes sets of different binding partners, wherein each set includes multiple copies of one type of binding partner which differs from the binding partners present in all other sets of binding partners.

The terms "polypeptide," "peptide", and "protein" are used interchangeably herein and refer to a polymer of amino acid residues. The terms apply to amino acid polymers in which one or more amino acid residue is an artificial chemical analogue of a corresponding naturally occurring amino acid, as well as to amino acid polymers containing only naturally occurring amino acids. The term "binding protein" refers to any protein binding partner other than an antibody, as defined above.

The terms "nucleic acid" or "oligonucleotide" or grammatical equivalents herein refer to at least two nucleotides covalently linked together. A nucleic acid refers to a single-stranded or double stranded polymer and will generally contain phosphodiester bonds, although in some cases, as outlined below, nucleic acid analogs are included that may have alternate backbones, comprising, for example, phosphoramide or peptide nucleic acid backbones.

The terms "nucleic acid molecule encoding" "DNA sequence encoding" and "DNA encoding", as used herein refer to the order or sequence of deoxyribonucleotides along a strand of deoxyribonucleic acid. The order of these deoxyribonucleotides determines the order of amino acids along the polypeptide (protein) chain. The DNA sequence thus codes for the amino acid sequence.

The term, "diagnostic platform", as used herein, refers to any device and/or method that may be used to detect and/or identify a biological organism. For example, a diagnostic platform may be used to detect and/or identify an hMPV viral particle.

The term, "intradermal injection cartridge", as used herein, refers to any device that is capable of delivering a measured dose of a composition into the intradermal region of the skin. For example, a cartridge may intradermally administer an hMPV MAb such that circulating hMPV viral particles are detecting by observing the development of a conventional histamine-mediated inflammation reaction (i.e., for example, a "wheal and flare" reaction).

The term, "porous material", as used herein, refers to any material that is permeable to fluids.

The term, "electrical field" as used herein, refers to the relative positioning of a positive electrode and negative electrode such that an electrical potential is created between the electrodes. Consequently, any particle within the electrical potential is considered to be "under the influence of an electric field".

The term "electric potential", as used herein, refers to the potential energy of a unit positive charge at a point in an electric field that is reckoned as the work which would be required to move the charge to its location in the electric field from an arbitrary point having zero potential (as one at infinite distance from all electric charges) and that is roughly analogous to the potential energy at a given elevation in a gravitational field.

The term "solid support", as used herein, refers to any composition and/or material that is capable of immobilizing a compound including, but not limited to, an antigen (i.e., for example, an hMPV) or an antibody (i.e., for example, an antibody reactive with an hMPV). A solid support may include, but is not limited to, beads, strips, wells, microchannels etc.

The term "nitrocellulose test strip", as used herein, refers to any device or composition comprising nitrocellulose wherein a compound may be detected and/or identified.

The term "ferrofluid", as used herein, refers to any composition comprising iron to which another compound (i.e., for example, an antibody) may be attached. Ferrofluids may also have attached purification molecules (i.e., for example, biotin) to facilitate their removal and isolation from a biological sample.

An "integrated microfluidic system" is a microfluidic system in which a plurality of fluidic operations are performed. In one embodiment, the results of a first reaction in the microfluidic system are used to select reactants or other reagents for a second reaction or assay. The system will typically include a microfluidic substrate, and a fluidic interface for sampling reactants or other components. A detector and a computer are often included for detecting reaction products and for recording, selecting, facilitating and monitoring reactions in the microfluidic substrate.

A "microfluidic device" is an apparatus or component of an apparatus having microfluidic reaction channels and/or chambers. Typically, at least one reaction channel or chamber will have at least one cross-sectional dimension between about 0.1 μm and about 500 μm.

A "reaction channel" is a channel (in any form, including a closed channel, a capillary, a trench, groove or the like) on or in a microfluidic substrate (a chip, bed, wafer, laminate, or the like having microfluidic channels) in which two or more components are mixed. The channel will have at least one region with a cross sectional dimension of between about 0.1 μm and about 500 μm.

A "reagent channel" is a channel (in any form, including a closed channel, a capillary, a trench, groove or the like) on or in a microfluidic substrate (a chip, bed, wafer, laminate, or the like having microfluidic channels) through which components are transported (typically suspended or dissolved in a fluid). The channel will have at least one region with a cross sectional dimension of between about 0.1 μm and about 500 μm.

A "material transport system" is a system for moving components along or through microfluidic channels. Exemplar transport systems include electrokinetic, electroosmotic, and electrophoretic systems (e.g., electrodes in fluidly connected wells having a coupled current and/or voltage controller), as well as micro-pump and valve systems.

A "fluidic interface" in the context of a microfluidic substrate is a component for transporting materials into or out of the substrate. The interface can include, e.g., an electropipettor, capillaries, channels, pins, pipettors, sippers or the like for moving fluids into the microfluidic substrate.

BRIEF DESCRIPTION OF THE FIGURES

FIGS. 2 (C & D) present exemplary data showing hMPV isolation and identification in LLC-MK2 shell vial cell cultures by using MAbs 48 hours after inoculation of two different NPA samples. Panel C: Single infected cells. Panel D: A plaque of infected cells with small syncytial formations.

FIG. 4 (E-H) presents exemplary data showing the typing of hMPV strains by IFA and type-specific MAbs on respiratory cells from NPA. Panel E: Type A hMPV NPA stained with hMPV Type A MAb; Panel F: Type A hMPV NPA stained with hMPV Type B MAb; Panel G: Type B hMPV NPA stained with hMPV Type A MAb; Panel H: Type B hMPV NPA stained with hMPV Type B MAb.

DETAILED DESCRIPTION OF THE INVENTION

Figure 1:
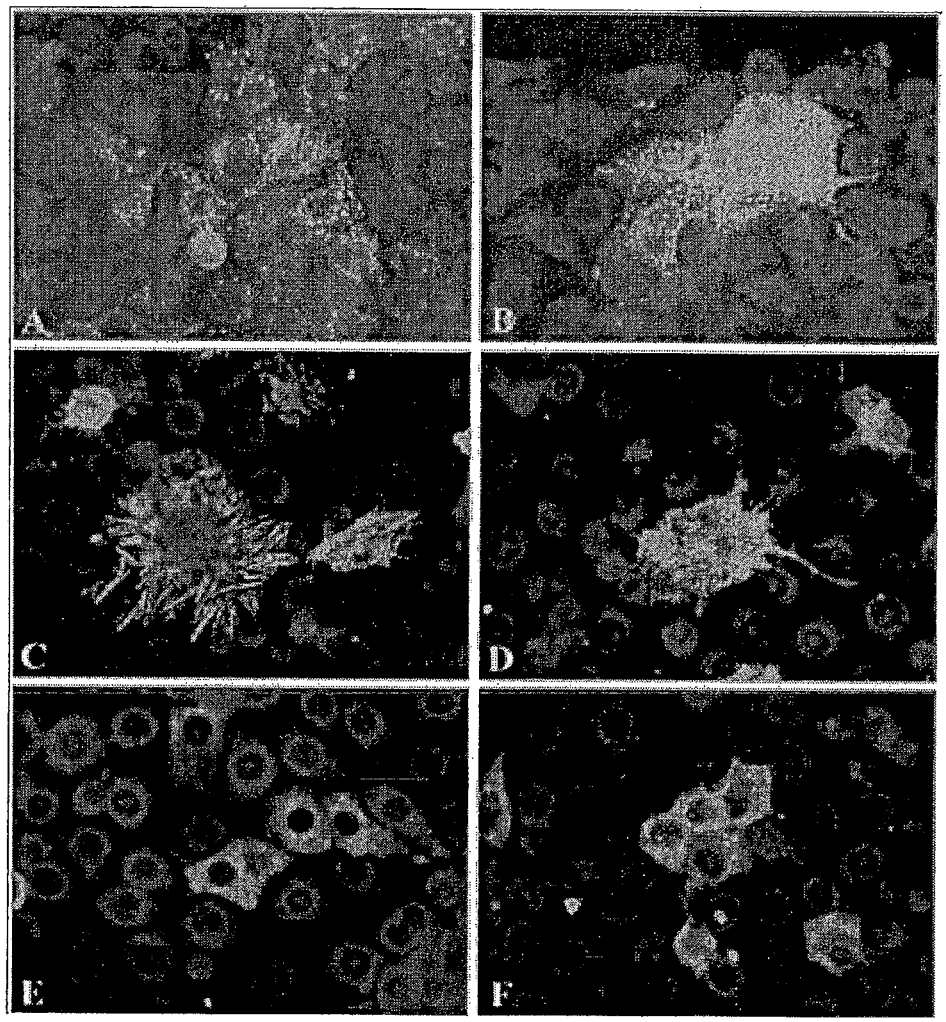
FIG. 1 presents exemplary data showing patterns of IFA staining of MAbs to hMPV on hMPV-infected LLC-MK2 cell cultures. Panels A & B: Granular patterns (hMPV MAbs from Clone C2C10). Panels C & D: Filamentous patterns (hMPV MAbs from Clone C2D11). Panels E & F: Foamy patterns (hMPV MAbs from Clone T3H11).
Figure 2:
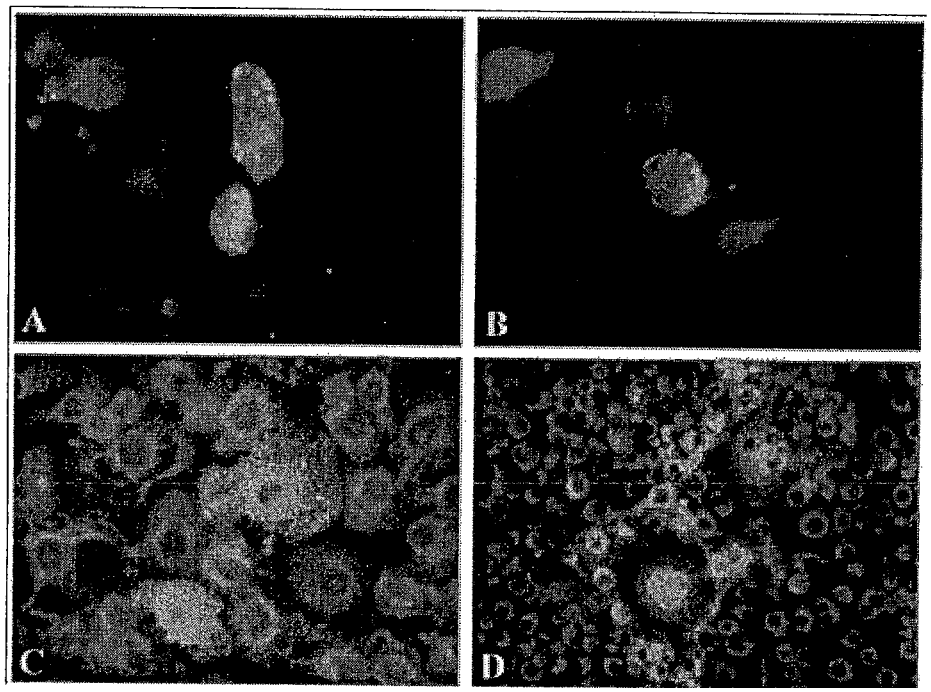
FIGS. 2 (A & B) present exemplary data showing direct fluorescent antibody (DFA) staining of respiratory mucosal cells from two different NPAs.

This invention is related to the detection and identification of viruses. In one embodiment, the virus comprises a metapneumovirus. In one embodiment, the virus infects a mammal. In one embodiment, the infection may be identified using an antibody. In particular, the antibodies are monoclonal antibodies produced from a hybridoma cell culture.

At least two genetic lineages of hMPV have been identified, with both lineages circulating during the same season (i.e., for example, Type A and Type B). The surface glycoproteins, G and SH show the most divergence between the two main lineages, with the G protein being more divergent than observed between human RSV A and B lineages. Unlike other current diagnostic hMPV technologies, the present invention has successfully provided monoclonal antibodies that detect and identify a specific type of hMPV (i.e., for example, Type A or Type B) and does not have detectable cross-reactivity with other respiratory viruses or an avian metapneumovirus.

I. Metapneumovirus

Known avian metapneumoviruses belong to four different types (A through D), with type C being the closest to hMPV. Jacobs et al., "Subtype B avian metapneumovirus resembles subtype A more closely than subtype C or human metapneumovirus with respect to the phosphoprotein, and second matrix and small hydrophobic proteins" Virus Res. 92:171-178 (2003); and Njenga et al., "Metapneumovirus in birds and humans" Virus Res. 91:163-169 (2003). It cannot be excluded that other, as-yet-unidentified, types of hMPV strains exist that may have similarity to avian metapneumovirus types A, B and D. In one embodiment, the present invention contemplates a monoclonal antibody that detects only human metapneumovirus epitopes, and without detectable cross-reactivity to other respiratory viruses or the avian metapneumovirus subtypes.

Some monoclonal antibodies raised to a human metapneumovirus types may have significant cross-over reactivity with avian metapneumovirus, or other respiratory viruses. Consequently, it must be empirically shown that a specific hMPV MAb is at least two-fold more reactive than with other respiratory viruses or the avian metapneumoviruses.

All human metapneumovirus (hMPV) strains recovered until now in different countries of the five continents have been classified into two major clusters, referred to as types A and B, on the basis of sequencing and phylogenetic analysis of genes L, N, F, or P. Boivin et al., "Virological features and clinical manifestations associated with human pneumovirus: A new paramyxovirus responsible for acute respiratory-tract infections in all age groups" J Infect Dis 186:1330-1334 (2002); Boivin et al., "Global genetic diversity of human metapneumovirus fusion gene" Emerg Infect Dis 10:1154-1157 (2004); Van den Hoogen et al., "A newly discovered human pneumovirus isolated from young children with respiratory tract disease" Nat Med 7:719-724 (2001); and Van den Hoogen et al., "Antigenic and genetic variability of human metapneumoviruses" Emerg Infect Dis 10:658-665 (2004). The recently identified human metapneumovirus (hMPV) is the only member of the genus Metapneumovirus that infects humans (family Paramyxoviridae, subfamily Paramyxovirinae). As discussed above, the genus Metapneumovirus also includes avian pneumoviruses A, B, C, and D.

II. Monoclonal Antibodies

In one embodiment, the present invention contemplates a composition comprising a monoclonal antibody raised against a human metapneumovirus (i.e., for example, Type A or Type B human metapneumovirus). In one embodiment, the monoclonal antibody is at least two-fold more reactive with human metapneumovirus than with an avian metapneumovirus, or other respiratory viruses. In one embodiment, the human metapneumovirus monoclonal antibody is reactive against type A human metapneumovirus. In another embodiment, the human metapneumovirus monoclonal antibody is reactive against type B human metapneumovirus. Although it is not necessary to understand the mechanism of an invention, it is believed that the development of monoclonal antibodies having specificity to human metapneumovirus are capable of typing all strains previously characterized by sequencing and phylogenetic analysis.

The recent discovery of hMPV as a major respiratory pathogen of infants and young children has been made possible by means of RT-PCR. Studies thus far published have mostly been conducted using this molecular approach. The present invention contemplates hMPV-specific MAbs that will now allow the routine use of direct fluorescence antibody (DFA) staining for hMPV detection in NPAs. Advantages of using hMPV-specific MAbs versus an RT-PCT assay include, but are not limited to, quick sample turn-around time and simple laboratory procedures. In addition, MAbs are capable of reacting with all four hMPV subtypes and proves the ability of these reagents to detect all known hMPV strains Bastien et al., "Sequence analysis of the N, P, M, and F genes of Canadian human metapneumovirus" *Virus Res.*, 93:51-62 (2003); Boivin et al., "Global genetic diversity of human metapneumovirus fusion gene" *Emerg. Infect. Dis.* 10:1154-1157 (2004); Mackay et al., "Use of the P gene to genotype human metapneumovirus identifies 4 viral subtypes", *J. Infect. Dis.* 190:1913-1918 (2004); and van den Hoogen et al., "Antigenic and genetic variability of human metapneumovirus" *Emerg. Infect. Dis.* 10:658-665 (2004). This simple diagnostic approach cannot be attained using RT-PCR, which requires a specific and technically difficult procedure for each diagnostic test.

Development of monoclonal antibodies having specificity for a human metapneumovirus (hMPV MAbs) is an important advance in the field of rapid direct diagnosis of respiratory tract viral infections. Following the introduction of hybridoma technology, MAbs to other respiratory viruses were developed and made commercially available. MAbs to hMPV, however, were not available.

Since then, DFA staining using MAbs has become the most rapid technique for direct diagnosis of acute respiratory infections, taking only 2 to 3 hours to perform. Expertise in reading the results of DFA assays and good-quality smears of respiratory cells are preferred for reliable performance of the DFA assay. In parallel, molecular assays aimed at amplifying viral genomes directly in clinical samples have been developed and compared to DFA staining for diagnosis of respiratory viral infections (i.e., for example, RT-PCR). Rovida et al., "Monoclonal Antibodies versus reverse transcription-PCR for detection of respiratory viruses in a patient population with respiratory tract infections admitted to hospital" *J Med Virol.* 75:336-347 (2005). These comparisons, however, did not include hMPV MAbs because of their commercial unavailability.

Initially developed RT-PCR protocols were unable to detect type B strains in clinical samples. van de Hoogen et al., "Prevalence and clinical symptoms of human metapneumovirus infection in hospitalized patients" *J. Infect. Dis.* 188:1571-1577 (2003). This deficiency was corrected by the identification of a second primer that is capable of identifying type B strains. Sararini et al., "Detection and pathogenicity of human metapneumovirus respiratory infection in pediatric Italian patients during a winter-spring season" *J Clin Virol* 35:59-68 (2006). Consequently, it is necessary to perform RT-PCR protocols using both sets of primer pairs to detect all hMPV types and/or subtypes. Although it is not necessary to understand the mechanism of an invention, it is believed that type-specific hMPV MAbs as contemplated by the present invention perform better than RT-PCR methods when the RT-PCR primers are not carefully selected based upon conserved regions of the genome.

Further, available research regarding hMPV MAb development has not reported any ability to differentiate between hMPV Type A viral antigens and hMPV Type B viral antigens. Landry et al., "Detection of human metapneumovirus in clinical samples by immunofluorescence staining of shell vial centrifugation cultures prepared from three different cell lines" *J Clin Microbiol.* 43:1950-1952 (2005); and De Jong et al., "Virus causing respiratory tract illness in susceptible mammals" United States Patent Application Publ. No. 2005/0053919 (2005). Specifically, De Jong et al. contemplates using antibodies that have sufficient cross-reactivity between human metapneumovirus and avian metapneumovirus such that an antibody raised to a human metapneumovirus may be used to detect an avian metapneumovirus and vice versa. Clearly, these hMPV MAbs have limited and/or no use for clinical diagnosis and treatment.

In one embodiment, the present invention contemplates hMPV MAbs comprising a wide reactivity with all known hMPV subtypes. In one embodiment, the hMPV MAb has selectivity for hMPV Subtype A. In another embodiment, the hMPV MAb has selectivity for hPMV Subtype B. In one embodiment, an hMPV MAb selectively detects an hMPV antigen using a nasopharengeal aspirate (NPA) smear. In another embodiment, an hMPV MAb selectively detects an hMPV antigen using an LLC-MK2 shell vial cell cultures inoculated with NPAs.

In one embodiment, Type A and Type B hMPV strains (1-PV 03/01 6621 and I-PV 03/04 4702, respectively) were propagated in LLC-MK2 cell cultures. Gerna et al., "Changing circulation rate of human metapneumovirus strains and types among hospitalized pediatric patients during three consecutive winter-spring seasons" *Arch Virol* 150:2365-2375 (2005). In another embodiment, virus suspensions were first clarified and then concentrated by ultracentrifugation. Although it is not necessary to understand the mechanism of an invention, it is believed that the clarification and ultracentrifugation steps results in an hMPV MAb preparation that has little or no non-specific binding.

Then, BALB/C mice were inoculated according to standard procedures. Percivalle et al., "Rapid detection of human metapneumovirus strains in nasopharyngeal aspirates and shell vial cultures by monoclonal antibodies" *J Clin Microbiol* 43:3443-3446 (2005). Following fusion of mouse spleen cell suspensions with Sp2/0Ag14 myeloma cells, the MAbs expressed by the hybridomas were tested for specific reactivity with hMPV by enzyme-linked immunosorbent assay and the indirect fluorescent antibody (IFA) assay. Following cloning and subcloning, MAbs previously selected for specific reactivity with hMPV were tested for type specificity by IFA using these Type A and Type B hMPV strains.

hMPV MAb specific reactivity to hMPV proteins was determined using Western blots of sucrose-purified reference hMPV strains CAN83 (Type A) and CAN75 (Type B). These reference strains are reported in: Peret et al., "Characterization of human metapneumoviruses isolated from patients in North America" *J Infect Dis* 185:1660-1663 (2002). Further, hMPV MAbs were tested by IFA on LLC-MK2 cells, which were infected with recombinant human parainfluenza virus type 1 expressing the hMPV fusion (F), small hydrophobic (SH), and the attachment glycoprotein (G) of either CAN83 (Type A) and CAN75 (Type B). Newman et al., "Sequence analysis of the Washington/1964 strain of human parainfluenza virus type 1 (HPIV1) and recovery and characterization of wild-type recombinant HPIV1 produced by reverse genetics" *Virus Genes* 24:77-92 (2002); and Skiadopoulos et al., "The two major human metapneumovirus genetic lineages are highly related antigenically, and the fusion (F) protein is a major contributor to this antigenic relatedness" *J Virol* 78:6927-6937 (2004). Both type-specific MAbs were found to react with the F protein of the same virus type by both IFA and Western blot (i.e., an hMPV Type A MAb reacts with an hMPV Type A F protein and an hMPV Type B MAb reacts with an hMPV Type B F protein).

Two hMPV MAbs (i.e., for example, clones F4A1 (IgG1) and CB7F3 (IgG1) were reactive by both DFA and ELISA assays with either type A or type B hMPV strains. In one embodiment, clone F4A1 is selective for hMPV subtypes A1 and A2. In one embodiment, clone CB7F3 is selective for hMPV subtypes B1 and B2. Gerna et al., "Simultaneous detection and typing of human metapneumovirus strains in nasopharyengeal secretions and cell cultures by monoclonal antibodies. *J Clin Virol* 35:113-115 (2006) The hMPV MAbs were further tested for cross-reactivities with conventional respiratory viruses (i.e., for example, influenza viruses A and B, parainfluenza virus types 1-4, human respiratory syncytial virus, human adenovirus, human coronaviruses 229, OC43 and NL63, and rhinoviruses). No cross-reactivity with any known respiratory viruses was detected for either one of the two selected MAbs. Further, these hMPV MAbs show little or no non-specific staining (i.e., background interference). hMPV MAbs created according to the above described protocol, were tested by DFA using 67 NPA samples. Specifically, 24 hMPV strains were typed by hMPV MAbs using duplicate NPA slides. The data showed that sixteen (16) strains were found to belong to Type A, and eight (8) strains were found to belong to Type B. See Table I. These results exactly matched those obtained by sequencing and phylogenetic analysis. Gerna et al., supra.

In parallel, MAbs specific for Type A or Type B human metapneumovirus were also used to test eighteen (18) NPA samples positive for different respiratory viruses. The data clearly show that no cross-reactivity with any of the other respiratory viruses tested was found, thereby demonstrating that hMPV MAbs as contemplated by the present invention have a 100% specificity for hMPV. In addition, hMPV type-specific MAbs were tested against respiratory cells from twenty-five (25) NPA samples negative for respiratory viruses. Again, no non-specific reactivity with uninfected respiratory cells was detected. See Table I.

TABLE I hMPV typing of 24 hMPV-positive NPA samples by DFA using MAbs specific for either Type A or Type B hMPV compared to typing by phylogenetic analysis

| Respiratory virus | No. NPAs tested | Typing by hMPV MAbs | |
|---|---|---|---|
| | | Type A | Type B |
| hMPV type A[a] | 16 | 16 | 0 |
| hMPV type B[a] | 8 | 0 | 8 |
| Influenza virus A | 2 | 0 | 0 |
| Influenza virus B | 2 | 0 | 0 |
| Parainfluenza virus 1-3 | 3 | 0 | 0 |
| Respiratory syncytial virus | 3 | 0 | 0 |
| Adenovirus | 2 | 0 | 0 |
| Human coronaviruses | 3 | 0 | 0 |
| Rhinoviruses | 3 | 0 | 0 |
| None (cells from NPA) | 25 | 0 | 0 |

In addition, 18 NPAs positive for different respiratory viruses and 25 NPA samples negative for respiratory viruses were tested as controls.
[a]As typed by sequencing and phylogenetic analysis.

Furthermore, some NPA samples positive for hMPV using RT-PCR were re-typed using MAbs having specificity for human metapneumovirus as contemplated by the present invention using LLC-MK2 cell cultures (i.e., for example, by using a shell vial centrifugation technique). While 12/12 (100%) of samples inoculated as fresh NPAs were recovered in cell cultures and typed, only 8/25 (32%) samples thawed once or twice, could be typed. Thus, both hMPV recovery and typing are optimally achieved by inoculating fresh samples onto cell cultures.

Figure 3:
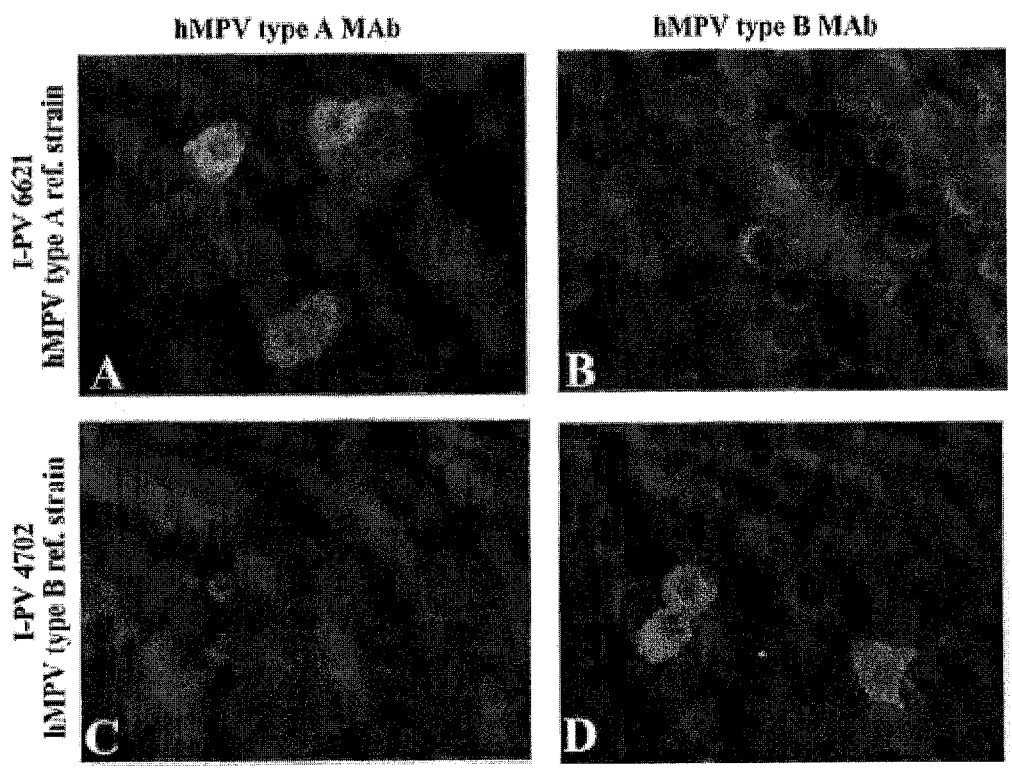
FIG. 3 presents exemplary data showing the typing of reference hMPV strains in LLC-MK2 cell cultures by type-specific MAbs and indirect immunofluorescence (IFA) 24 h p.i. Panel A: Type A reference strain I-PV 03/01 6621 stained with hMPV Type A MAb. Panel B: Type A reference strain I-PV 03/01 6621 stained with hMPV Type B MAb. Panel C: Type B reference strain I-PV 03/04 4702 stained with hMPV Type A MAb. Panel D: Type B reference strain I-PV 03/4 4702 stained with hMPV Type B MAb.
Figure 4:
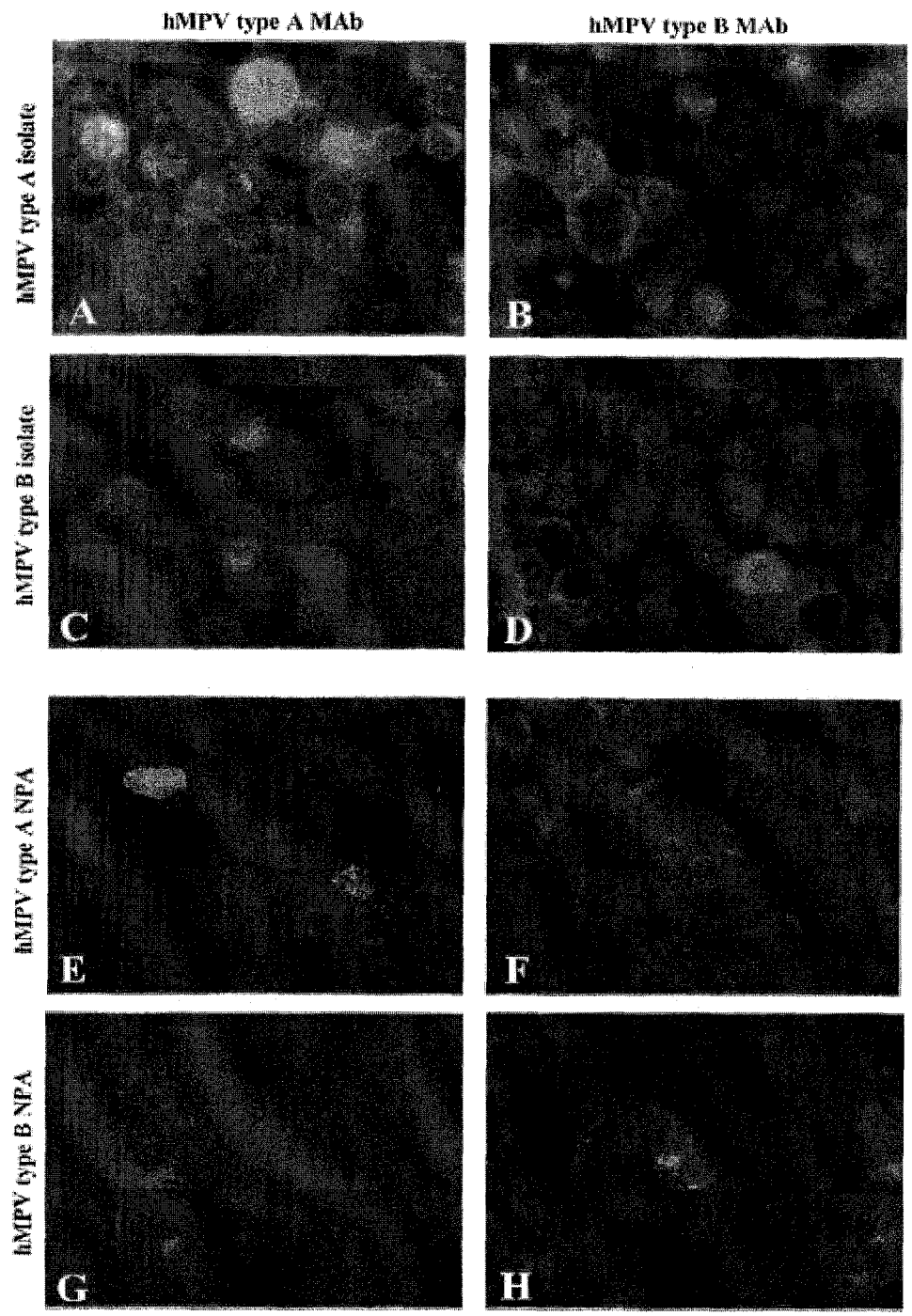
FIG. 4 (A-D) presents exemplary data showing the typing of two hMPV isolates recovered in LLC-MK2 cell cultures after an 48 hour incubation by TA and MAbs. Panel A: Type A isolate stained with hMPV Type A MAb; Panel B: Type A isolate stained with hMPV Type B MAb; Panel C: Type B isolate stained with hMPV Type A MAb. Panel D: Type B isolate stained with hMPV Type B MAb.

Morphological patterns of the two type-specific MAbs in cell cultures infected with reference strains are shown. See FIG. 3. In addition, IFA patterns observed in respiratory tract cells from hMPV-infected NPA samples, as well as in LLC-MK2 cell cultures following hMPV isolation, are shown for both Type A and Type B hMPV strains. FIGS. 4 (A-D) and FIGS. 4 (E-H), respectively. The staining intensity ranged from 1+ to 4+ in different cells, while the staining pattern was similar to the granular pattern of one of three MAbs included in the pool for hMPV detection. Percivalle et al., "Rapid detection of human metapneumovirus strains in nasopharyngeal aspirates and shell vial cultures by monoclonal antibodies" *J Clin Microbiol* 43:3443-3446 (2005).

Although it is not necessary to understand the mechanism of an invention, it is believed that the development of MAbs having specificity to hMPV are capable of classifying all hMPV strains tested into Type A or Type B, thereby exactly matching results given by sequencing and phylogenetic analysis. It is further believed that since both Type A and Type B hMPV have been found to circulate at different rates in different years hMPV typing, the hMPV MAb's contemplated herein may be useful for epidemiological research and prediction. Gerna et al., "Changing circulation rate of human metapneumovirus strains and types among hospitalized pediatric patients during three consecutive winter-spring seasons" *Arch Virol* 150:2365-2375 (2005).

hMPV typing by MAbs is highly preferable over typing by phylogenetic analysis in terms of practicality, rapidity and cost-effect benefits. Given the 100% sensitivity and specificity of type-specific MAbs with respect to hMPV detection by the MAb pool, detection and typing of new hMPV strains by MAbs may be performed simultaneously in viral diagnostic laboratories. Percivalle et al., "Rapid detection of human metapneumovirus strains in nasopharyngeal aspirates and shell vial cultures by monoclonal antibodies" *J Clin Microbiol* 43:3443-3446 (2005); and Gerna et al., supra.

III. Diagnostics

Some embodiments of the present invention contemplate direct antibody detection and identification of hMPV virus proteins that represent an improvement of immunological identification of hMPV strains was achieved by direct fluorescent antibody (DFA) staining of cells from NPA samples. Ebihara et al., "Detection of human metapneumovirus antigens in nasopharyngeal secretions by an immunofluorescent-antibody test" *J Clin Microbiol* 43:1138-1141 (2005).

A wide spectrum of clinical symptoms is associated with hMPV infection. In the general community, hMPV-infected adults mainly suffer from upper respiratory tract illnesses (common cold-like symptoms) such as cough, rhinorrhea, hoarseness, sore throat and sometimes fever. In hospitalized children, patients with underlying disease, immunocompromised individuals, and fragile elderly, hMPV disease may be more severe, involving the lower respiratory tract. Clinical diagnoses may range from rhinopharyngitis to bronchitis and pneumonia, and some patients may be admitted to intensive care units. In addition, diarrhea, vomiting, rash, febrile seizures, feeding difficulties, conjunctivitis and otitis media have all been reported. The wide spectrum of hMPV-induced illnesses reported thus far are similar to those caused by RSV and influenza virus infections.

Some embodiments of the present invention contemplate the administration of monoclonal antibodies having specificity for a human metapneumovirus. In one embodiment, the monoclonal antibody administration is given to a subject such that an hMPV infection is prevented (i.e., prophylactic administration). In one embodiment, the monoclonal antibody administration is given to a subject such that an existing hMPV infection is reduced, ameliorated, and/or eliminated.

MAb detection of hMPV antigens was reported using inoculated cell cultures. Percivalle et al., "Rapid detection of human metapneumovirus strains in nasopharyngeal aspirates and shell vial cultures by monoclonal antibodies" *J Clin Microbiol* 43:3443-3446 (2005). Although sensitivity and negative predictive value of MAbs were somewhat lower than those achieved by RT-PCR, rapidity of turnaround time, simplicity of test performance, and MAb specificity provide advantages that favor this immunological approach over conventional detection techniques.

An hMPV MAb raised to a matrix protein (MAb-8; MAB8510, Chemicon International, Temecula, Calif.) was reported as capable of detecting hMPV in shell vial centrifugation cultures. Landry et al., "Detection of human metapneumovirus in clinical samples by immunofluorescence staining of shell vial centrifugation cultures prepared from three different cell lines" *J Clin Microbiol* 43:1950-1952 (2005). MAb-8 was unable to detect hMPV in clinical samples, however, because of uncontrollable non-specific staining (i.e., for example, resulting from background cellular material and/or other viruses). This nonspecific background staining made reading very tedious and interpretation was difficult. Specific recommendations for using MAb-8 included experience in distinguishing specific versus nonspecific staining and to always include both positive and negative controls.

Rapid immunological diagnosis of conventional respiratory virus infections is currently performed by direct fluorescent antibody (DFA) staining of respiratory cells present in nasopharyngeal aspirate (NPA) samples using virus-specific monoclonal antibodies (MAbs). Rovida et al., "Monoclonal Antibodies versus reverse transcription-PCR for detection of respiratory viruses in a patient population with respiratory tract infections admitted to hospital" *J Med. Virol.* 75:336-347 (2005). Therefore, MAbs with specific reactivity to hMPV antiens within biological samples (i.e., for example, NPAs) are needed, although they are not yet commercially available. This invention discloses MAbs specific for Type A hMPV and Type B hMPV and their use for DFA staining of NPA samples and virus identification in shell vial cell cultures.

A. Diagnostic Platforms

Some embodiments of the present invention can provide a high-throughput, simple, and rapid diagnostic clinical tool having many advantages over RT-PCR protocols. For instance, the use of hMPV MAbs can be incorporated into many types of immunological assay devices and techniques (i.e., for example, diagnostic platforms) that are already commercially available.

1. Cartridges

In one embodiment, the present invention contemplates a diagnostic platform comprising an intradermal injection of an hMPV MAb for diagnostic testing. Similar to determining the immunity status of the animal against tuberculosis and the immediate hypersensitivity status of Type I allergic diseases, a prefilled container administers hMPV MAb into a subject either having, or at risk for, an hMPV infection. A positive reaction is then noted upon redness, swelling, or tenderness at the injection site indicating that the MAb injection initiated an inflammatory reaction due to the presence of hMPV antigens within the subject.

An intradermal injection is made by delivering the substance into the epidermis and upper layer of the dermis. Below the dermis layer is subcutaneous tissue (also sometimes referred to as the hypodermis layer) and muscle tissue, in that order. There is considerable variation in the skin thickness both between individuals and within the same individual at different sites of the body. Generally, the outer skin layer, epidermis, has a thickness between 500-200 microns, and the dermis, the inner and thicker layer of the skin, has a thickness between 1.5-3.5 mm. Therefore, a needle cannula that penetrates the skin deeper than about 3.0 mm has a potential of passing through the dermis layer of the skin and making the injection into the subcutaneous region, which may result in an insufficient immune response, especially where the substance to be delivered intradermally has not been indicated for subcutaneous injection. Also, the needle cannula may penetrate the skin at too shallow a depth to deliver the substance and result in a "wet injection" because of reflux of the substance from the injection site.

For example, an intradermal needle assembly compatible with a prefillable container having a reservoir capable of storing hMPV MAb for injection into the skin of an animal includes a hub portion being attachable to the prefillable container storing the substance, a needle cannula supported by the hub portion and having a forward tip extending away from the hub portion, and a limiter portion surrounding the needle cannula and extending away from the hub portion toward the forward tip of the needle cannula, the limiter including a generally flat skin engaging surface extending in a plane generally perpendicular to an axis of the needle cannula and adapted to be received against the skin of the animal to administer an intradermal injection of the substance, the needle forward tip extending beyond the skin engaging surface a distance approximately 0.5 mm to 3.0 mm wherein the limiter portion limits penetration of the needle into the dermis layer of skin of the animal so that the vaccine is injected into the dermis layer of the animal. Alchas et al., "Intradermal needle" U.S. Pat. No. 6,843,781 (2005). (herein incorporated by reference).

2. Cell Based Assays hMPV may be detected using a diagnostic platform comprising cell culture (i.e., for example, tMK cells (RIVM, Bilthoven, The Netherlands) technique using a plurality of well plates containing glass slides (Costar, Cambridge, UK). The cells are incubated with a medium as described below supplemented with 10% fetal bovine serum (BioWhittaker, Vervier, Belgium). Before hMPV inoculation, the plates were washed with PBS and supplied with Eagle's MEM with Hanks' salt (ICN, Costa mesa, Calif.) supplemented with 0.52/liter gram $NaHCO_3$, 0.025 M Hepes (Biowhittaker), 2 mM Iglutamine (Biowhittaker), 200 units/liter penicilline, 200 µg/liter streptomycin (Biowhittaker), 1 gram/liter lactalbumin (Sigma-Aldrich, Zwindrecht, The Netherlands), 2.0 gram/liter D-glucose (Merck, Amsterdam, The Netherlands), 10 gram/liter peptone (Oxoid, Haarlem, The Netherlands) and 0.02% trypsin (Life Technologies, Bethesda, Md.).

Plate inoculation may be performed with a supernatant of the nasopharyngeal aspirate samples (i.e., for example, 0.2 ml per well in triplicate) followed by centrifuging at 840×g for one hour. After inoculation, the plates are incubated at 37° C. for a maximum of 14 days changing the medium once a week and cultures were checked daily for cytopathic effects (CPE). After 14 days, cells can be scraped from a second passage and incubated for another 14 days. This step may be repeated for a third passage. The glass slides were used to demonstrate the presence of the virus by indirect IFA.

CPE is generally observed after a third passage, at day 8 to 14, depending on the isolate. CPE induced by hMPV is virtually indistinguishable from that caused by hRSV or hPIV in tMK or other cell cultures. However, hRSV induces CPE starting around day 4. CPE may be characterized by syncytia formation, after which the cells showed rapid internal disruption, followed by detachment of cells from the monolayer. If CPE is difficult to observe, IFA may be used to confirm the presence of the virus in these cultures. De Jong et al., "Virus causing respiratory tract illness in susceptible mammals" United States Patent Application 2005/0053919 (2005) (herein incorporated by reference).

3. Porous Media Support Material

In one embodiment, an hMPV can be retained on a diagnostic platform comprising a porous media under the influence of an electrical field with fluid flow. In this manner, an hMPV can be concentrated on the porous media with a low electrical field with fluid flow. In one embodiment, the virus can then be removed from the porous media by reducing or shutting off the electrical field. Although it is not necessary to understand the mechanism of an invention, it is believed that unique sets of conditions (i.e., solution flow rate and electrical field strength) are capable of immobilizing a virus using a given media and solution composition.

For example, elution electrophoresis uses a flow-through porous media with an applied electrical field. The electrical field causes the selective retention of compounds (i.e., for example, viral protein and/or nucleic acids). The retention of these compounds is dependent on the flow rate (velocity) and electrical field strength in a given porous media. The chemical and physical nature of the porous media plays a role in the separation process. Very selective separations are possible using this technology because the electrical field strength, flow velocity, and porous media can be varied for each separation. Individual components in the mixture can be retained to varying degrees by the separation conditions used. The degree of retention is determined by the chemical and physical properties of each component. Cole K. D., "Concentration and size-fractionation of nucleic acids and viruses in porous media" U.S. Pat. No. 5,707,850 (1998)(herein incorporated by reference).

The flow rate of the solution through the porous media is also a variable in this process. The flow rate can be held constant or varied. Flow rate can be changed in steps or continuously (a gradient) during the separation process.

In one embodiment, the media comprises a porous and fairly neutral material and includes, but is not limited to, Sephadex®, dextran, cellulose, acrylamide, polymeric particles, or silica. In one embodiment, the material comprises beads and may be applied with a column. In another embodiment, the material is applied on membranes, and/or thin layers.

The pH, ionic strength, and composition of the solution can also be modified during the separation process. The pH of the solution determines the charge and electrophoretic mobility of each component. It is possible to lower the pH significantly, so that the proteins will become positively charged and not be retained, while nucleic acids will still be negatively charged and retained on the porous media. The ionic strength and ionic composition of the solution will influence the electrical field strength and influence interactions of components with the porous media. The solution can be varied in its composition to include additives that vary the interactions of the components with the porous media (such as detergents and zwitterions). Modification of the composition of the solution during the separation is therefore a variable that can be used to achieve selective separations.

The electrical field strength and polarity can also be changed during the separation (i.e., for example, a negative field or a positive field). The field can be changed continuously or in a step-wise fashion. Alternating and pulsed electrical fields can also be used. Any direction of pulsing may be used, including reverse flow, right angles, orthogonal, etc. Although it is not necessary to understand the mechanism of an invention, it is believed that low electrical fields used to separate the DNA are advantageous because they do not result in column heating which can lead to temperature gradients that ruin resolution and can denature delicate biological molecules. Further, low electrical fields have very little effect on the retention of proteins so that they pass through the column.

Recovery of products can be automated, thereby making the process commercially viable. The methods can be used for protein recovery, removal of unwanted proteins, and/or isolation of viruses (i.e., for example, human metapneumovirus). The process can also be used to separate nucleic acids from proteins and/or viruses from proteins.

Elution electrophoretic separation includes, but is not limited to, a zone of porous media, electrodes for applying an electrical field across the media, a means of flowing solution through the porous media (such as a pump), a device to introduce sample to be separated (i.e., for example, an automated microsyringe), and a device to collect the solution.

For example, one elution electrophoresis system utilizes a porous packed bed providing protein separation and a flow photometer or colorimeter for continuous monitoring of the eluate. In one embodiment, an elution electrophoresis system is capable of rapid, high-resolution analysis of hMPV proteins such that they may be detected by a variety of post-separation methods. For example, such a system may comprise a cooled separation column (i.e., for example, 3 mm in diameter and 40 cm long) containing polyacrylamide beads. hMPV protein samples are introduced, via a microsyringe, through a septum at the column midpoint. Typical analyses requires an electrophoresis time of about 30 min at 1200 V. Scott et al., "Automated elution electrophoresis: a potential clinical tool" *Clin Chem.* 1975 21(9):1217-20 (1975).

4. Dipsticks and Other Solid Supports

Another diagnostic platform for the identification of hMPV types and subtypes comprises devices and materials enabling the detection of hMPV in biological materials, and is particularly suited for screening large amounts of samples. One embodiment comprises one or more hMPV-specific monoclonal antibodies and a solid support. In one embodiment, the solid support comprises a microtiter plate, wherein the microtiter plate is optionally coated with the monoclonal antibodies. In another embodiment, the solid support comprises a test strip, wherein the test strip is optionally coated with the monoclonal antibodies. In one embodiment, the test strip comprises nitrocellulose. In one embodiment, a secondary anti-mouse antibody that is coupled with an enzyme and its substrate or any other molecular compound for a detection reaction (i.e., for example, a peroxidase-labeled anti-mouse IgG antibody, TMB or any other peroxidase substrate).

In another embodiment, the method provides a dipstick format and is without need of radioactive tracers, enzymes or substrates and may require no more than a single step. This one-step procedure involves the capture of an hMPV viral protein with one of the hMPV-specific MAbs which are immobilized on a solid support (i.e., for example, a nitrocellulose test strip). These captured hMPV viral proteins may then be detected directly by a second antibody. In one embodiment, a detector complex results in the formation of colored spots on the test strip which are visible in less than 30 minutes depending on the concentration of the test sample. The spots are a permanent record of the test result and, longer exposures increase the sensitivity of the test without generating higher background. Korth et al., "Immunological detection of prions" U.S. Pat. No. 6,765,088 (2004)(herein incorporated by reference).

The biological material containing the hMPV sample can be insoluble or soluble in buffer or body fluids. The biological material can be derived from any part of the body (i.e., for example, from the brain, or tissue sections). Homogenates may be prepared or any body fluid (i.e., for example, cerebrospinal fluid, urine, saliva, or blood). In the case of body fluids, fluid-resident cells (i.e., for example, white blood cells) can be purified and analyzed either in immunohistochemistry or as a homogenate.

5. Microfluidics

Some embodiments of the present invention contemplate a diagnostic platform comprising a high-throughput microfluidic device and/or method comprising hMPV MAbs. In one embodiment, the device is capable of contacting hMPV MAbs with hMPV viral particles, such that the viral particles are detected, and identified within the microfluidic device Although it is not necessary to understand the mechanism of an invention, it is believed that suitable microfluidic substrate materials are generally selected based upon their compatibility with the conditions present in the particular operation to be performed by the device. For example, such conditions can include, but are not limited to, extremes of pH, temperature, salt concentration, and application of electrical fields. Additionally, substrate materials are also selected for their inertness to critical components of an analysis or synthesis to be carried out by the device.

In one embodiment, a substrate material may be selected from the group comprising glass, quartz, silicon, or other polymeric substrates (i.e., for example, plastics). In the case of conductive or semi-conductive substrates, it is occasionally desirable to include an insulating layer on the substrate. This is preferable when the device incorporates electrical elements, e.g., electrical fluid direction systems, sensors and the like. In the case of polymeric substrates, the substrate materials may include, but are not limited to, rigid, semi-rigid, non-rigid, opaque, semi-opaque or transparent, depending upon the use for which they are intended. For example, devices which include, for example, an optical, spectrographic, photographic or visual detection element, will generally be fabricated, at least in part, from transparent materials to allow, or at least, facilitate that detection. Alternatively, transparent windows of, e.g., glass or quartz, are optionally incorporated into the device for these types of detection elements. Additionally, the polymeric materials optionally have linear or branched backbones, and can be crosslinked or non-crosslinked. Examples of polymeric materials include, but are not limited to, polydimethylsiloxanes (PDMS), polyurethane, polyvinylchloride (PVC) polystyrene, polysulfone, polycarbonate, or polymethylmethacrylate (PMMA).

In certain embodiments, the microfluidic substrate comprises one or more microchannels for flowing reactants and products. In one embodiment, at least one of these channels typically has a very small cross sectional dimension, e.g., in the range of from about 0.1 μm to about 500 μm. In one embodiment, a cross-sectional dimension of the channels may range of from about 1 μm to about 200 μm, preferably in the range of from about 0.1 μm to about 100 μm, but more preferably in the range of about 1 μm to 100 μm. In order to maximize the use of space on a substrate, alternative geometries, including but not limited to serpentine, saw tooth or other channel geometries, may be used. Although it is not necessary to understand the mechanism of an invention, it is believed that these alternative geometries facilitate separation of reaction products or reactants and increase the channel length within a defined surface area. Substrates may be of essentially any size, with area typical dimensions of about 1 $cm^2$ to 10 $cm^2$.

Some embodiments of the present invention contemplate a microfluidic device comprising one or more chambers, channels or the like, wherein the chambers and/or channels are fluidly connected to allow transport of fluid among the chambers and/or channels. By "microfluidic" is generally meant fluid systems, e.g., channels, chambers and the like, typically fabricated into a solid typically planar substrate, and wherein these fluid elements have at least one cross-sectional dimension in the range of from about 0.1 to about 500 μm. Typically, the cross sectional dimensions of the fluid elements will range from about 1 μm to about 200 μm. A "chamber" will typically, though not necessarily, have a greater volume than a channel, typically resulting from an increased cross-section having at least one dimension from about 10 to about 500 μm, although, as for channels, the range can span, e.g., 0.1 to about 500 μm. Although generally described in terms of channels and chambers, it will generally be understood that these structural elements are interchangeable, and the terms are used primarily for ease of discussion. By "fluidly connected", or "in fluid communication", or "in liquid communication" is meant a junction between two regions, e.g., chambers, channels, wells etc., through which fluid freely passes. Such junctions may include ports or channels, which can be clear, i.e., unobstructed, or can optionally include valves, filters, and the like, provided that fluid freely passes through the junction when desired.

In one embodiment, the present invention contemplates a method providing a microfluidic device that is used for separating biological particles (i.e., for example, viral particles or antibodies). In one embodiment, a virus membrane protein (i.e., for example, an hMPV membrane protein) may be complexed with a capture bead within a reaction channel. In one embodiment, diagnostic reagents (i.e., for example, an hMPV monoclonal antibody) may be stored in a reagent well. Other solutions, such as buffers for material transport, and or reagents may be stored in other wells. In one embodiment, an electropipettor channel is fluidly connected to the reaction channel thereby providing an automated high-throughput diagnostic system.

In some embodiments, the viral proteins may be attached to capture beads (i.e., for example, posts, magnetic beads, polymer beads or the like) and electrokinetically transported to a bead capture area. In one embodiment, an electropipettor channel provides an appropriately labeled monoclonal antibodies that is also transported to the bead capture area. In one embodiment, the labeled monoclonal antibody attaches to the viral proteins thereby allowing detection and identification of the virus when the antibody/viral protein complex is eluted. Optionally, the antibody/viral protein complex may be washed from the bead capture area using a loading buffer and optionally electrophoresed through a size separation microchannel. Knapp et al., "Microfluidic devices and methods for separation" U.S. Pat. No. 6,444,461 (2002)(herein incorporated by reference).

Alternatively, hMPV may be captured using isolation fluids such as those designed to be used with the CellTracks® AutoPrep System (Immunicon, Huntingdon, Pa.). Owen et al., "Magnetic-polymer particles" U.S. Pat. No. 4,795,698 (1989) (herein incorporated by reference). For example, a ferrofluid comprising a magnetic core coated with BSA, can be conjugated with hMPV MAbs for capturing hMPVs. Ferrofluid particles are colloidal, which permit long incubations without ferrofluid settling within a reaction chamber. In one embodiment, the present invention contemplates a ferrofluid comprising an hMPV-specific MAb attached to a particle comprising an oxide and magnetite, having an average diameter of approximately 145 nm. In one embodiment, greater than 85% of the oxide is $Fe_3O_4$. In one embodiment, the magnetite is approximately 80% (w/w). In one embodiment, the particle comprises a magnetic susceptibility of approximately 125 emu/gm, wherein there are approximately $4\times10^{11}$ particles/mg lion, and further wherein each particle comprises approximately 3 fg $Fe_3O_4$ and 1 fg BSA. In one embodiment, the hMPV MAb ferrofluid may further comprise biotinylated molecules. In one embodiment, the ferrofluid comprises approximately 15,000 small biotinylated molecules/particle. In another embodiment, the ferrofluid comprises approximately 5,000 large biotinylated molecules/particle. In yet another embodiment, the ferrofluid comprises approximately 50-150 µg monobiotinylated MAb/mg Iron. In still yet another embodiment, the ferrofluid comprises approximately 10 nanomoles biotin-FITC/mg Iron.

Many microfabrication techniques may be used to manufacture these microscale elements onto the surface of a substrate. For example, lithographic techniques are generally employed in fabricating microscale devices using substrates including, but not limited to, glass, quartz or silicon. Lithographic techniques are common in the semiconductor manufacturing industries such as photolithographic etching, plasma etching or wet chemical etching. Ghandi, S. K., In: *VLSI Principles: Silicon and Gallium Arsenide*, NY, Wiley (see, esp. Chapter 10). Alternatively, micromachining methods such as laser drilling, air abrasion, micromilling and the like may be employed. Polymeric substrates may be manufactured by techniques including, but not limited to, injection molding or stamp molding methods. Large numbers of polymeric substrates may be produced using: i) rolling stamps producing a large sheet of microscale substrate; or ii) polymer microcasting techniques where the substrate is polymerized within a micromachined mold. Parce et al., "Controlled fluid transport in microfabricated polymeric substrates" U.S. Pat. No. 5,885,470 (1999) (herein incorporated by reference).

IV. Preparation of Binding Partners

Some embodiments of the present invention contemplate the binding of monoclonal antibodies with binding partners (i.e., for example, viral particles) for detection and identification. In one embodiment, the viral particles may include, but are not limited to, nucleic acids and/or proteins. In one embodiment, an hMPV MAb may become a binding partner with an hMPV viral particle.

A. Nucleic Acids

Nucleic acids for use as binding partners in this invention can be produced or isolated according to any of a number of methods. In one embodiment, the nucleic acid can be an isolated naturally occurring nucleic acid (e.g., genomic DNA, cDNA, mRNA, etc.). Methods of isolating naturally occurring nucleic acids have been reported. (see, e.g., Sambrook et al. (1989) Molecular Cloning—A Laboratory Manual (2nd Ed.), Vol. 1 3, Cold Spring Harbor Laboratory, Cold Spring Harbor, N.Y.).

Nucleic acids useful in the invention can also be amplified from a nucleic acid sample (i.e., for example, an hMPV nucleic acid sample). A number of amplification techniques have been described, but the polymerase chain reaction (PCR) is the most widely used. U.S. Pat. Nos. 4,683,202, 4,683,195, 4,800,159, and 4,965,188 (all of which are herein incorporated by reference). Briefly, PCR entails hybridizing two primers to substantially complementary sequences that flank a target sequence in a nucleic acid. A repetitive series of reaction steps involving template denaturation, primer annealing, and extension of the annealed primers by a DNA polymerase results in the geometric accumulation of the target sequence, whose termini are defined by the 5' ends of the primers. As denaturation is typically carried out at temperatures that denature most DNA polymerases (e.g., about 93° C.-95° C.), a thermostable polymerase, such as those derived from *Thermus thermophilus, Thermus aquaticus* (Taq), or *Thermus flavus*, is typically used for extension to avoid the need to add additional polymerase for each extension cycle.

In one embodiment, the nucleic acid is created de novo, e.g., through chemical synthesis. In one embodiment, nucleic acids (e.g., oligonucleotides) are chemically synthesized according to the solid phase phosphoramidite triester method. Beaucage et al., *Tetrahedron Letts.* 22:1859-1862 (1981). In one embodiment, the nucleic acid is synthesized using an automated synthesizer. Needham-VanDevanter et al., *Nucleic Acids Res.* 12:6159-6168 (1984). Purification of oligonucleotides, where necessary, is typically performed by either native acrylamide gel electrophoresis or by anion-exchange HPLC. Pearson et al., *J. Chrom.* 255:137-149 (1983). The sequence of the synthetic oligonucleotides can be verified using chemical degradation. Maxam et al., *Meth. Enzymol.* 65:499-560 (1980).

B. Antibodies/Antibody Fragments

In one embodiment, antibodies or antibody fragments for use as binding partners can be produced by a number of methods. Harlow & Lane, In: *Antibodies: A Laboratory Manual*, Cold Spring Harbor Laboratory (1988); and Asai, "Antibodies in Cell Biology", In: *Methods in Cell Biology* Vol. 37: Academic Press, Inc. N.Y (1993). In one embodiment, antibodies are produced by immunizing an animal (e.g. a rabbit) with an immunogen containing the epitope to be detected. A number of immunogens may be used to produce specifically reactive antibodies. Recombinant proteins are the preferred immunogens for the production of the corresponding monoclonal or polyclonal antibodies. Naturally occurring protein may also be used either in pure or impure form. Synthetic peptides are also suitable and can be made using standard peptide synthesis chemistry. Barany et al., "Solid-Phase Peptide Synthesis"; pp. 3-284 In: *The Peptides: Analysis, Synthesis, Biology. Vol. 2: Special Methods in Peptide Synthesis, Part A.*; Merrifield et al., *J. Am. Chem. Soc.,* 85:2149-2156 (1963); and Stewart et al., In: *Solid Phase Peptide Synthesis,* 2nd ed. Pierce Chem. Co., Rockford, Ill. (1984).

Many methods of production of polyclonal antibodies have been previously reported. In brief, an immunogen is mixed with an adjuvant and an animal is immunized. The animal's immune response to the immunogen preparation is monitored by taking test bleeds and determining the titer of reactivity to the immunogen. When appropriately high titers of antibody to the immunogen are obtained, blood is collected from the animal and an antiserum is prepared. If desired, the antiserum can be further fractionated to enrich for antibodies having the desired reactivity. (See Harlow et al., supra).

Many methods of production of monoclonal antibodies have also been reported. Briefly, spleen cells from an animal immunized with a desired antigen are immortalized, commonly by fusion with a myeloma cell. Kohler et al., *Eur. J. Immunol.* 6:511-519 (1976). Alternative methods of immortalization include, but are not limited to, transformation with Epstein Barr Virus, oncogenes, or retroviruses. Colonies arising from single immortalized cells are screened for production of antibodies of the desired specificity and affinity for the antigen, and yields of the monoclonal antibodies produced by such cells can be enhanced by various techniques, including injection into the peritoneal cavity of a vertebrate host. Alternatively, DNA sequences encoding a monoclonal antibody or a binding fragment thereof can be isolated by screening a DNA library from human B cells. Huse et al., *Science,* 246: 1275 1281 (1989). Such isolated sequences can then be expressed recombinantly.

In one embodiment, antibody fragments (i.e., for example, hMPV antibody fragments), may include, but are not limited to, single chain antibodies (scFv or others) and can be produced/selected using phage display technology. Although it is not necessary to understand the mechanism of an invention, it is believed that the ability to express antibody fragments on the surface of viruses that infect bacteria (bacteriophage or phage) makes it possible to isolate a single binding antibody fragment from a library of greater than $10^{10}$ nonbinding clones. It is further believed that to express antibody fragments on the surface of phage (phage display), an antibody fragment gene is inserted into the gene encoding a phage surface protein (pIII) and the antibody fragment-pIII fusion protein is displayed on the phage surface. McCafferty et al., *Nature* 348: 552-554 (1990); and Hoogenboom et al., *Nucleic Acids Res.* 19:4133-4137 (1991).

In one embodiment, functional antibody fragments on the surface of the phage can be used to separate out non-binding phage by antigen affinity chromatography. McCafferty et al., *Nature* 348:552-554 (1990). Although it is not necessary to understand the mechanism of an invention, it is believed that depending on the affinity of the antibody fragment, enrichment factors of 20 fold-1,000,000 fold may be obtained for a single round of affinity selection. By infecting bacteria with the eluted phage, however, more phage can be grown and subjected to another round of selection. In this way, an enrichment of 1000 fold in one round can become 1,000,000 fold in two rounds of selection. Thus, even when enrichments are low, multiple rounds of affinity selection can lead to the isolation of rare phage. Marks et al., *J. Mol. Biol.* 222:581-597 (1991). Since selection of the phage antibody library on antigen results in enrichment, the majority of clones bind antigen after as few as three to four rounds of selection. Thus, only a relatively small number of clones (several hundred) need to be analyzed for binding to antigen.

Naturally occurring human antibodies can be produced without prior immunization by displaying very large and diverse V-gene repertoires on phage (Marks et al., supra). In one embodiment, natural $V_H$ and $V_L$ repertoires present in human peripheral blood lymphocytes are isolated from unimmunized donors by PCR. The V-gene repertoires are spliced together at random using PCR to create a scFv gene repertoire which is then cloned into a phage vector to create a library of 30 million phage antibodies. It is also possible to isolate antibodies against cell surface antigens by selecting directly on intact cells. The antibody fragments are highly specific for the antigen used for selection and have affinities in the 1 µM to 100 nM range. Griffiths et al., *EMBO J.* 12:725-734 (1993). Larger phage antibody libraries result in the isolation of more antibodies of higher binding affinity to a greater proportion of antigens.

C. Proteins, Peptides and Fragments Thereof

In one embodiment, the binding partner can be a protein (i.e., for example, a hMPV viral protein). In one embodiment, suitable proteins, peptides and fragments thereof include, but are not limited to, viral proteins (i.e., for example, M, L, N etc.), receptors (e.g., cell surface receptors), receptor ligands (e.g., cytokines, growth factors, etc.), transcription factors and other nucleic acid binding proteins, as well as members of binding pairs, such as biotin-avidin.

Binding proteins useful in the invention can be isolated from natural sources, mutagenized from isolated proteins, or synthesized de novo. Isolation methods for naturally occurring proteins include, but are not limited to, conventional protein purification methods including ammonium sulfate precipitation, affinity chromatography, column chromatography, or gel electrophoresis. R. Scopes, (1982) In: *Protein Purification*, Springer-Verlag, N.Y.; and Deutscher (1990) Methods in Enzymology Vol. 182: Guide to Protein Purification, Academic Press, Inc. N.Y. Although it is not necessary to understand the mechanism of an invention, it is believed that where a protein binds a target reversibly, affinity columns bearing the target can be used to affinity purify the protein. Alternatively the protein can be recombinantly expressed with a HIS-Tag and purified using $Ni^{2+}$/NTA chromatography.

In another embodiment, a binding protein can be chemically synthesized using standard chemical peptide synthesis techniques. Where the desired subsequences are relatively short, the molecule may be synthesized as a single contiguous polypeptide. Where larger molecules are desired, subsequences can be synthesized separately (in one or more units) and then fused by condensation of the amino terminus of one molecule with the carboxyl terminus of the other molecule thereby forming a peptide bond. This is typically accomplished using the same chemistry (e.g., Fmoc, Tboc) used to couple single amino acids in commercial peptide synthesizers.

In one embodiment, a solid phase synthesis may be used in which a C-terminal amino acid of a peptide sequence is attached to an insoluble support. In one embodiment, the remaining amino acids in the sequence are sequentially added. Barany et al., (1962) Solid-Phase Peptide Synthesis; pp. 3-284, In: *The Peptides: Analysis, Synthesis, Biology. Vol. 2: Special Methods in Peptide Synthesis, Part A.*; Merrifield et al. (1963) J. Am. Chem. Soc., 85: 2149-2156; and Stewart et al. (1984) Solid Phase Peptide Synthesis, 2nd ed. Pierce Chem. Co., Rockford, Ill.

In one embodiment, a binding protein can also be produced using recombinant DNA methodology. Generally this involves generating a DNA sequence that encodes the binding protein, placing the DNA sequence in an expression cassette under the control of a particular promoter, expressing the protein in a host, isolating the expressed protein and, if necessary, renaturing the protein.

In one embodiment, DNA encoding for binding proteins can be prepared by any suitable method as described above, including, for example, cloning and restriction of appropriate sequences or direct chemical synthesis by methods such as: i) the phosphotriester method of Narang et al. (1979) Meth. Enzymol. 68: 90-99; ii) the phosphodiester method of Brown et al. (1979) Meth. Enzymol. 68: 109 151; iii) the diethylphosphoramidite method of Beaucage et al. (1981) Tetra. Lett., 22: 1859 1862; and iv) the solid support method of U.S. Pat. No. 4,458,066 (all of which are herein incorporated by reference).

In one embodiment, DNA encoding a desired binding protein(s) can be expressed in a variety of host cells, including, but not limited to, *E. coli*, other bacterial hosts, yeast, and various higher eukaryotic cells, such as the COS, CHO and HeLa cells lines and myeloma cell lines. The DNA sequence encoding the binding protein is operably linked to appropriate expression control sequences for each host to produce an expression construct. For *E. coli*, examples of appropriate expression control sequences include a promoter such as the T7, trp, or lambda promoters, a ribosome binding site and preferably a transcription termination signal. For eukaryotic cells, such control sequences can include a promoter, an enhancer derived, e.g., from immunoglobulin genes, SV40, cytomegalovirus, etc, and a polyadenylation sequence, and may include splice donor and acceptor sequences.

In one embodiment, an expression vector can be transferred into the chosen host cell by such methods as calcium chloride transformation for *E. coli* and calcium phosphate treatment or electroporation for mammalian cells. Cells transformed with the expression vector can be selected by resistance to antibiotics conferred by genes contained on the plasmids, such as the amp, gpt, neo and hyg genes.

Once expressed, the recombinant binding proteins can be purified using conventional techniques.

EXPERIMENTAL

The following examples are intended only as illustrative embodiments contemplated by the present invention and should not be considered limiting in any respect.

Example I

Preparation Of hMPV Hybridomas

This example provides one embodiment regarding the preparation of hybridomas that produces monoclonal antibodies directed to hMPV. The stains used below were based upon a sequencing and phylogenetic analysis of hMPV strains circulating in northern Italy in the 2001 through 2004 winter-spring seasons. Gema et al, "Changing circulation rate of human metapneumovirus strains and styles among hospitalized pediatric patients during three consecutive winter-spring seasons" *Arch. Virol.* (In Press).

Viral strains belonging to hMPV types (A and B) and subtypes (A1-A2 and B1-B2) were isolated and propagated onto LLC-MK2 cell cultures. After 5 to 10 passages, the various hMPV strains were released from infected cultures. Infectivity was demonstrated by showing a 100% cytopathic effect 5 days postinfection at titers of $\geq 10^7$ 50% tissue culture infective doses/ml. Following clarification, hMPV prototypes A and B were pelleted by ultracentrifugation, reaching titers of $<10^9$ 50% tissue culture infective doses/ml.

These virus preparations were inoculated intramuscularly into BALB/c mice four times according to the following: i) the first virus inoculum was administered using complete Freund's adjuvant; ii) three (3) weeks after the first inoculum, the second inoculum was administered using incomplete Freund's adjuvant; iii) five (5) weeks after the first inoculum, the third inoculum was administered in saline; and iv) six (6) weeks after the first inoculum, the fourth inoculum was administered in saline.

A mouse spleen cell suspension was prepared and fused with Sp2/0Ag14 myeloma cells. The hybridoma supernatants were tested for reactivity with hMPV by enzyme-linked immunosorbent assay and the indirect fluorescent antibody (IFA) assay. Reactive hybridomas were identified, cloned and subcloned twice. Cross-reactivities with conventional respiratory viruses (i.e., for example, influenza viruses A and B, parainfluenza virus types 1 to 4, human respiratory syncytial virus, human adenoviruses, human coronaviruses 229E and OC43, and rhinoviruses) were tested by IFA assay. Hybridoma clones showing a variable degree of cross-reactivity with human respiratory syncytial virus and were excluded from diagnostic use.

hMPV-specific MAbs showed three major IFA patterns on hMPV-infected LLC-MK2 cell cultures: i) granular (FIGS. 1A and 1B; ii) filamentous (FIGS. 1C and 1D); and iii) foamy (FIGS. 1E and 1F). This pool of three MAbs, including: i) clone C2C10 having reactivity with A1, A2, B1, and B2 hMPV subtype strains (immunoglobulin G1 [IgG1]), ii) clone C2D11 having reactivity with A1, A2, B1, and B2 hMPV subtype strains (IgG1); and iii) clone T3H11 having reactivity with A1, A2, B1, and B2 hMPV subtype strains (IgG2a), each representative of a different staining pattern and reactive by both IFA and enzyme-linked immunosorbent assays, was used for diagnostic purposes. None of these hMPV MAbs were reactive with avian metapneumoviruses A and B (data not shown; avian metapneumovirus kindly provided by Ilaria Capua, Istituto Zooprofilattico delle Tre Venezie, Padua, Italy). Although it is not necessary to understand the mechanism of an invention, it is hypothesized that the differences in staining patterns between the different hMPV MAbs may be due to a selective affinity for different viral proteins.

Example II

Detection of hMPV Using Hybridoma Monoclonal Antibodies

Forty NPA samples collected during the winter-spring season of 2003-2004 from 40 infants and young children admitted to the hospital because of an episode of acute respiratory infection were retrospectively tested for hMPV with MAbs by (i) using frozen smears of NPA samples for DFA staining and (ii) inoculating frozen NPA samples, previously tested for conventional respiratory viruses, onto shell vial cell cultures.

Cells isolated from respiratory secretions had been previously used for preparation of multiple smears, which were fixed with methanol-acetone and stored at −80° C. After thawing, the smears were stained with MAbs to hMPV and, in parallel, with a high-titer guinea pig hyperimmune serum. The pool of three MAbs was used for retrospective DFA staining of the 40 frozen NPA smears from respiratory secretions. See Table II; FIG. 2A and FIG. 2B.

TABLE II

Diagnostic value of DFA using MAbs to hMPV with respect to RT-PCR

| Reactivity with | No. of samples tested by RT-PCR (%) | | |
|---|---|---|---|
| MAbs to hMPV | Positive | Negative | Total |
| Positive | 17 (73.9) | 1 (5.9) | 18 (45.0) |
| Negative | 6 (26.1) | 16 (94.1) | 22 (55.) |
| Total | 23[a] | 17[b] | 40[c] |

[a]Positive predictive value, 94.4%.
[b]Negative predictive value, 72.7%.
[c]Agreement, 82.5%.

Specimens had been previously tested by RT-PCR for hMPV genes N and F and found to be either positive (n=23; 18 type A and 5 type B strains) or negative (n=17). On the whole, DFA staining detected as positive 17/23 NPAs found to be positive by RT-PCR (12 subtype A2, 2 subtype B1, and 3 subtype B2), while 6 subtype A2 strains were negative. In addition, DFA staining detected as negative 16/17 NPAs found to be negative by RT-PCR (one subtype A2 strain was positive by DFA staining in very few cells). In the six RT-PCR-positive DFA-negative samples, no correlation was observed between a weak PCR signal and lack of DFA signal, suggesting the presence of extracellular virus not detectable by DFA staining in the relevant NPAs.

In addition, four original NPAs (among those examined by DFA staining) stored frozen at −80° C. and previously found to be positive by RT-PCR were inoculated onto LLC-MK2 shell vial cell cultures and incubated for 48 h at 37° C. Following fixation with methanol-acetone and immunostaining with the same pool of MAbs to hMPV, the four hMPV strains were easily identified. Virus strains were detected in cell cultures as either multiple single infected cells or small plaques with small syncytial formations. (FIG. 2C and FIG. 2D, respectively).

We claim:

1. A composition comprising a solid support and one or more human metapneumovirus (hMPV)-specific monoclonal antibodies selected from the group consisting of an hMPV monoclonal antibody produced by C2C10, an hMPV monoclonal antibody produced by F4A1, and an hMPV monoclonal antibody produced by CB7F3.

2. The composition of claim 1, wherein said solid support comprises a test strip.

3. The composition of claim 2, wherein said test strip is attached to a dipstick.

4. The composition of claim 1, wherein said solid support comprises a microtitre plate.

5. The composition of claim 4, wherein said plate is filled with said one or more hMPV-specific monoclonal antibodies.

6. The composition of claim 1, wherein said solid support comprises a cell based assay.

7. The composition of claim 6, wherein said cell based assay comprises tMK cells.

8. The composition of claim 1, wherein said solid support further comprises an elution electrophoresis system.

9. The composition of claim 8, wherein said elution electrophoresis system comprises a porous material under the influence of an electrical field.

10. The composition of claim 9, wherein said porous material is selected from at least one of the group consisting of dextran, cellulose, acrylamide, polymeric particles, and silica.

11. The composition of claim 3, wherein said dipstick comprises at least one compound selected from the group consisting of radioactive tracers, enzymes, colloidal metals, and substrates.

12. The composition of claim 1, wherein said solid support comprises a microfluidic device.

13. The composition of claim 12, wherein said microfluidic device comprises a ferrofluid, wherein said antibodies are attached to said ferrofluid.

14. The composition of claim 12, wherein said microfluidic device comprises at least one microchannel in fluidic communication with at least one microchamber.

15. The composition of claim 2, wherein said test strip comprises a fluid flow.

16. The composition of claim 9, wherein said porous material comprises a fluid flow.

17. The composition of claim 12, wherein said microfluidic device comprises a fluid flow.

18. The composition of claim 2, wherein said test strip comprises nitrocellulose.

19. The composition of claim 1, wherein said one or more human metapneumovirus (hMPV)-specific monoclonal antibodies are fluorescently labeled.

20. The composition of claim 1, wherein said solid support further comprises a secondary anti-mouse antibody.

21. The composition of claim 20, wherein said secondary anti-mouse antibody is coupled with an enzyme/substrate complex.

22. The composition of claim 21, wherein said enzyme/substrate complex is a peroxidase-labeled anti-mouse IgG antibody and a peroxidase substrate.

23. A method for detecting the presence of human metapneumovirus in a sample, comprising:
contacting said sample with a solid support and one or more human metapneumovirus (hMPV)-specific monoclonal antibodies selected from the group consisting of an hMPV monoclonal antibody produced by C2C10, an hMPV monoclonal antibody produced by F4A1, and an hMPV monoclonal antibody produced by CB7F3, wherein said sample is contacted with said solid support under conditions such that said one or more hMPV-specific monoclonal antibodies binds to said human metapneumovirus.

24. The method of claim 23, wherein said solid support comprises a test strip.

25. The method of claim 24, wherein said test strip is attached to a dipstick.

26. The method of claim 23, wherein said solid support comprises a microtitre plate.

27. The method of claim 26, wherein said microtitre plate is filled with said one or more hMPV-specific monoclonal antibodies.

28. The method of claim 23, wherein said assay comprises a cell based assay.

29. The method of claim 28, wherein said cell based assay comprises tMK cells.

30. The method of claim 23, wherein said solid support further comprises an elution electrophoresis system.

31. The method of claim 30, wherein said elution electrophoresis system comprises a porous material under the influence of an electrical field.

32. The method of claim 31, wherein said porous material is selected from at least one of the group consisting of dextran, cellulose, acrylamide, polymeric particles, and silica.

33. The method of claim 25, wherein said dipstick comprises at least one compound selected from the group consisting of radioactive tracers, enzymes, colloidal metals, and substrates.

34. The method of claim 23, wherein said solid support comprises a microfluidic device.

35. The method of claim 34, wherein said microfluidic device comprises a ferrofluid, wherein said antibodies are attached to said ferrofluid.

36. The method of claim 34, wherein said microfluidic device comprises at least one microchannel in fluidic communication with at least one microchamber.

37. The method of claim 24, wherein said test strip comprises a fluid flow.

38. The method of claim 31, wherein said porous material comprises a fluid flow.

39. The method of claim 34, wherein said microfluidic device comprises a fluid flow.

40. The method of claim 24, wherein said test strip comprises nitrocellulose.

41. The method of claim 23, wherein said one or more human metapneumovirus (hMPV)-specific monoclonal antibodies are fluorescently labeled.

42. The method of claim 23, wherein said solid support further comprises a secondary anti-mouse antibody.

43. The method of claim 42, wherein said secondary anti-mouse antibody is coupled with an enzyme/substrate complex.

44. The method of claim 43, wherein said enzyme/substrate complex is a peroxidase-labeled anti-mouse IgG antibody and a peroxidase substrate.

* * * * *